US010398667B2

(12) United States Patent
Baroni et al.

(10) Patent No.: US 10,398,667 B2
(45) Date of Patent: *Sep. 3, 2019

(54) METHODS OF TREATING HAIR RELATED CONDITIONS

(71) Applicant: Nogra Pharma Limited, Dublin (IE)

(72) Inventors: Sergio Baroni, Villa d'adda (IT); Salvatore Bellinvia, Mendrisio (CH); Francesca Viti, Salorino (CH)

(73) Assignee: Nogra Pharma Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,436

(22) Filed: Jan. 16, 2018

(65) Prior Publication Data

US 2018/0369178 A1 Dec. 27, 2018

Related U.S. Application Data

(63) Continuation of application No. 14/969,939, filed on Dec. 15, 2015, now Pat. No. 9,901,557, which is a continuation of application No. 14/314,738, filed on Jun. 25, 2014, now abandoned, which is a continuation of application No. 13/201,790, filed as application No. PCT/EP2010/000939 on Feb. 16, 2010, now Pat. No. 8,796,334.

(60) Provisional application No. 61/287,461, filed on Dec. 17, 2009, provisional application No. 61/179,062, filed on May 18, 2009.

(30) Foreign Application Priority Data

Feb. 16, 2009 (EP) .................................. 09425056

(51) Int. Cl.
| | |
|---|---|
| *A61K 31/196* | (2006.01) |
| *A61Q 7/00* | (2006.01) |
| *A61Q 5/00* | (2006.01) |
| *C07C 233/54* | (2006.01) |
| *C07C 235/38* | (2006.01) |
| *A61K 8/42* | (2006.01) |
| *C07D 307/79* | (2006.01) |
| *A61Q 19/08* | (2006.01) |
| *A61Q 19/06* | (2006.01) |
| *A61Q 19/02* | (2006.01) |
| *C07D 319/08* | (2006.01) |

(52) U.S. Cl.
CPC .............. *A61K 31/196* (2013.01); *A61K 8/42* (2013.01); *A61Q 5/00* (2013.01); *A61Q 7/00* (2013.01); *A61Q 19/02* (2013.01); *A61Q 19/06* (2013.01); *A61Q 19/08* (2013.01); *C07C 233/54* (2013.01); *C07C 235/38* (2013.01); *C07D 307/79* (2013.01); *C07D 319/08* (2013.01); *A61K 2800/78* (2013.01)

(58) Field of Classification Search
CPC .... A61K 31/196; A61K 8/42; A61K 2800/78; A61Q 5/00; A61Q 7/00; A61Q 19/02; A61Q 19/06; A61Q 19/08; C07C 233/54; C07C 235/38; C07D 307/79; C07D 319/08
USPC ....................................................... 514/223.2
See application file for complete search history.

(56) References Cited

U.S. PATENT DOCUMENTS

| | | |
|---|---|---|
| 3,211,610 A | 10/1965 | Rogers |
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,015,249 B1 | 3/2006 | Vanden Heuvel et al. |
| 7,049,342 B2 | 5/2006 | Miyachi et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |

(Continued)

FOREIGN PATENT DOCUMENTS

| | | |
|---|---|---|
| EP | 0055689 A1 | 7/1982 |
| EP | 0102833 A1 | 3/1984 |

(Continued)

OTHER PUBLICATIONS

Ahnfelt-Ronne et al. (1990) "Clinical Evidence Supporting the Radical Scavenger Mechanism of 5-Aminosalicylic Acid," Gastroenterology, 98(5 Pt 1):1162-9.

(Continued)

*Primary Examiner* — Kristin A Vajda
(74) *Attorney, Agent, or Firm* — Goodwin Procter LLP

(57) ABSTRACT

Disclosed herein are methods for treating hair related disorders, including compounds that may be specific or modulate PPAR receptors.

16 Claims, 14 Drawing Sheets

(56) References Cited

U.S. PATENT DOCUMENTS

| | | |
|---|---|---|
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |
| 8,450,506 B2 | 5/2013 | Naccari et al. |
| 8,501,806 B2 | 8/2013 | Baroni et al. |
| 8,710,100 B2 | 4/2014 | Naccari et al. |
| 8,754,127 B2 | 6/2014 | Baroni et al. |
| 8,796,282 B2 | 8/2014 | Karnik |
| 8,796,334 B2 * | 8/2014 | Baroni ............... A61K 8/42 514/563 |
| 9,133,099 B2 | 9/2015 | Naccari et al. |
| 9,345,680 B2 | 5/2016 | Naccari et al. |
| 9,511,041 B2 | 12/2016 | Baroni et al. |
| 9,561,202 B2 | 2/2017 | Naccari et al. |
| 9,682,050 B2 | 6/2017 | Baroni et al. |
| 9,682,923 B2 | 6/2017 | Baroni et al. |
| 9,901,557 B2 * | 2/2018 | Baroni ............... A61K 8/42 |
| 9,913,817 B2 | 3/2018 | Baroni et al. |
| 10,016,381 B2 | 7/2018 | Naccari et al. |
| 10,137,101 B2 | 11/2018 | Baroni et al. |
| 2003/0113815 A1 | 6/2003 | Houseknecht et al. |
| 2003/0133875 A1 | 7/2003 | Kelly |
| 2003/0220374 A1 | 11/2003 | Needleman |
| 2003/0229083 A1 | 12/2003 | Debnath et al. |
| 2004/0034067 A1 | 2/2004 | MacPhee |
| 2004/0115127 A1 | 6/2004 | Wright et al. |
| 2004/0132110 A1 | 7/2004 | Desreumaux et al. |
| 2006/0013775 A1 | 1/2006 | Gristwood et al. |
| 2006/0159648 A1 | 7/2006 | Davis et al. |
| 2006/0177444 A1 | 8/2006 | Horizoe |
| 2006/0270635 A1 | 11/2006 | Wallace et al. |
| 2007/0086967 A1 | 4/2007 | MacDonald |
| 2007/0149804 A1 | 6/2007 | Woltering et al. |
| 2009/0042909 A1 | 2/2009 | Karnik |
| 2009/0048343 A1 | 2/2009 | Naccari et al. |
| 2009/0118357 A1 | 5/2009 | Naccari et al. |
| 2010/0305077 A1 | 12/2010 | Baroni et al. |
| 2011/0105748 A1 | 5/2011 | Bhuniya et al. |
| 2011/0152225 A1 | 6/2011 | Baroni et al. |
| 2011/0288058 A1 | 11/2011 | Baroni et al. |
| 2011/0288177 A1 | 11/2011 | Baroni et al. |
| 2012/0053244 A1 | 3/2012 | Baroni et al. |
| 2012/0053245 A1 | 3/2012 | Baroni et al. |
| 2012/0157417 A1 | 6/2012 | Baroni et al. |
| 2012/0316230 A1 | 12/2012 | Naccari et al. |
| 2013/0005813 A1 | 1/2013 | Naccari et al. |
| 2015/0045436 A1 | 2/2015 | Naccari et al. |
| 2015/0051285 A1 | 2/2015 | Baroni et al. |
| 2015/0087678 A1 | 3/2015 | Baroni et al. |
| 2015/0087708 A1 | 3/2015 | Baroni et al. |
| 2015/0148418 A1 | 5/2015 | Baroni et al. |
| 2015/0250749 A1 | 9/2015 | Giuliani et al. |
| 2015/0265514 A1 | 9/2015 | Giuliani et al. |
| 2015/0265562 A1 | 9/2015 | Naccari et al. |
| 2015/0265563 A1 | 9/2015 | Naccari et al. |
| 2016/0338927 A1 | 11/2016 | Baroni et al. |
| 2017/0056349 A1 | 3/2017 | Baroni et al. |
| 2017/0172956 A1 | 6/2017 | Baroni et al. |
| 2017/0312239 A1 | 11/2017 | Naccari et al. |
| 2018/0064667 A1 | 3/2018 | Baroni et al. |
| 2018/0065921 A1 | 3/2018 | Baroni et al. |
| 2018/0369178 A1 | 12/2018 | Baroni et al. |

FOREIGN PATENT DOCUMENTS

| | | |
|---|---|---|
| EP | 0115419 A2 | 8/1984 |
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1373906 A1 | 1/2004 |
| EP | 1389044 A1 | 2/2004 |
| EP | 1607103 A1 | 12/2005 |
| EP | 1274407 B1 | 3/2006 |
| EP | 1801093 B1 | 3/2009 |
| EP | 1448995 B1 | 1/2011 |
| EP | 2298321 A1 | 3/2011 |
| EP | 2107047 B1 | 9/2011 |
| GB | 767788 A | 2/1957 |
| GB | 1359560 | 7/1974 |
| JP | 2003-516310 A | 5/2003 |
| JP | 3425441 B2 | 7/2003 |
| JP | 3435651 B2 | 8/2003 |
| JP | 2004-528329 A | 9/2004 |
| JP | 2005-510733 A | 4/2005 |
| JP | 2009-242399 A | 10/2009 |
| WO | WO-1992/006690 A1 | 4/1992 |
| WO | WO-1993/014056 A1 | 7/1993 |
| WO | WO-1994/000135 A1 | 1/1994 |
| WO | WO-1995/031194 A1 | 11/1995 |
| WO | WO-1996/030016 A2 | 10/1996 |
| WO | WO-1997/025042 A1 | 7/1997 |
| WO | WO-1998/006387 A2 | 2/1998 |
| WO | WO-1998/043081 A1 | 10/1998 |
| WO | WO-1999/015520 A1 | 4/1999 |
| WO | WO-2000/059866 A1 | 10/2000 |
| WO | WO-2000/062766 A2 | 10/2000 |
| WO | WO-2001/002388 A1 | 1/2001 |
| WO | WO-2001/025181 A1 | 4/2001 |
| WO | WO-2001/079153 A1 | 10/2001 |
| WO | WO-2002/046161 A1 | 6/2002 |
| WO | WO-2002/077651 A1 | 10/2002 |
| WO | WO-2002/085123 A1 | 10/2002 |
| WO | WO-2002/095393 A2 | 11/2002 |
| WO | WO-2003/033481 A1 | 4/2003 |
| WO | WO-2003/043569 A2 | 5/2003 |
| WO | WO-2003/046580 A1 | 6/2003 |
| WO | WO-2003/048116 A2 | 6/2003 |
| WO | WO-2004/073622 A2 | 9/2004 |
| WO | WO-2005/012280 A1 | 2/2005 |
| WO | WO-2005/040102 A2 | 5/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/094618 A2 | 8/2008 |
| WO | WO-2008/104557 A1 | 9/2008 |
| WO | WO-2009/025854 A1 | 2/2009 |
| WO | WO-2009/080828 A2 | 7/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |
| WO | WO-2013/012662 A2 | 1/2013 |
| WO | WO-2013/064153 A1 | 5/2013 |
| WO | WO-2013/117744 A9 | 8/2013 |
| WO | WO-2013/156413 A1 | 10/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |
| WO | WO-2014/154683 A1 | 10/2014 |
| WO | WO-2016/154730 A1 | 10/2016 |
| WO | WO-2016/202341 A1 | 12/2016 |
| WO | WO-2017/046343 A1 | 3/2017 |
| WO | WO-2017/093444 A1 | 6/2017 |
| WO | WO-2017/144725 A1 | 8/2017 |

(56) References Cited

FOREIGN PATENT DOCUMENTS

OTHER PUBLICATIONS

Allgayer (2003) "Review Article: Mechanisms of Action of Mesalazine in Preventing Colorectal Carcinoma in Inflammatory Bowel Disease," Aliment Pharmacol Ther, 18(Suppl. 2):10-4.
Ameho et al., (1997) 'Prophylactic Effect of Dietary Glutamine Supplementation on Interleukin 8 and Tumor Necrosis Factor Alpha Production in Trinitrobenzene Sulphonic Acid Induced Colitis,' Gut, 41(4):487-93.
Australian Examination Report dated Jan. 31, 2014, for Application No. 2009321722 (9 pages).
Azhar, (2010), 'Peroxisome Proliferator-Activated Receptors, Metabolic Syndrome and Cardiovascular Disease,' Future Cardiol, 6(5):657-91 (NIH Public Access Author Manuscript).
Baker et al., (1962) "Potential Anticancer Agents. LXXVIII Nonclassical Antimetabolites. IV. Synthesis of Compounds Related to 4-(Iodoacetamido) Salicylic Acid, an Exo-Alkylating Irreversible Inhibitor," J Org Chem, 27(9):3283-95.
Bassaganya-Riera, et al "Activation of PPAR γ and δ by conjugated linoleic acid mediates protection from experimental inflammatory bowel disease," Gastroenterology, vol. 127, No. 3, pp. 777-791, 2004.
Baz et al. (2003) 'Oxidant / Antioxidant Status in Patients with Psoriasis,' Yonsei Med J, 44(6):987- 90.
Behshad et al., (2008) 'A Retrospective Case Series Review of the Peroxisome Proliferator-Activated Receptor Ligand Rosiglitazone in the Treatment of Atopic Dermatitis,' Arch Dermatol, 144(1):84-8.
Beilstein Database Beistein Institute zur Forderung der Chemischen Wissenschaften, Frankfurt an Main, DE XP002413839, Accession No. 2092096, J. Med. Chem., 22: 589 (1979).
Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).
Beilstein Database, Beilstein Institute for Organic Chemistry, Frankfurt an Main, DE, retrieved from XFIRE, Accession No. brn 2803076, J. Org. Chem., 14: 1013, 1018 (1949).
Beilstein Database, Beilstein Institute for Organic Chemistry, Frankfurt an Main, DE, retrieved from XFIRE, Accession No. brn 3199913, Chem. Ber., 46: 3978 (1913).
Beilstein Database, Beilstein Institute for Organic Chemistry, Frankfurt an Main, DE, retrieved from XFIRE, Accession No. brn 3200601, J. Chem. Soc., pp. 104, 111 (1935).
Beilstein Database, Beilstein Institute for Organic Chemistry, Frankfurt an Main, DE, retrieved from XFIRE, Accession No. brn 3268495, Justus Liebigs Ann. Chem., 463:60 (1924).
Beilstein Database, Beilstein Institute for Organic Chemistry, Frankfurt an Main, DE, retrieved from XFIRE, Accession No. brn 3296969, Chem. News J. Ind. Sci, 36: 269 (1877).
Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).
Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institute zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers et al., (2006) 'Oxidative Stress in the Pathogenesis of Skin Disease,' J Invest Dermatol, 126(2):2565-75.
Bongartz et al., (2005) 'Treatment of Active Psoriatic Arthritis with the PPARy Ligand Pioglitazone: An Open-Label Pilot Study,' Rheumatology, 44(1):126-9.
Broadwith (2009) "Enzyme Binds Both Sides of the Mirror," Chem World, Nov. 6, 2009, https://www.chemistryworld.com/news/enzyme-binds-both-sides-of-the-mirror/1016647.article (2 pages).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Brown et al., (1978) "Chimie Organique," C.R. Acad. Sc. Paris, t. 287:125-8.
Brunton et al., (1997) "A Role of Epidermal Growth Factor Receptor, c-Src and Focal Adhesion Kinase in an in vitro Model for the Progression of Colon Cancer," Oncogene, 14( 3):283-93.
Bull (2003) "The Role of Peroxisome Proliferator-Activated Receptor y in Colon Cancer and Inflammatory Bowel Disease," Arch Pathol Lab Med, 127(9):1121-3.
Casen Recordati Group, (2016), 'Cleen Ready-to-Use Enema, Summary of Product Characteristics Updated Jun. 16, 2016,' emc+, medicines.org.UK/emc, XP-002763390, <https://www.medicines.org.UK/emc/print-document?documentld=542> [retrieved Oct. 25, 2016] (5 pages).
Casen Recordati Group, (2016), 'Cleen Ready-to-Use Enema,' emc+, medicines.org.UK/emc, XP-002763391, <https://www.medicines.oro.UK/emc/history/542#version9> [retrieved Oct. 25, 2016] (2 pages).
Clark et al., (1989) "Validation of the General Purpose Tripos 5.2 Field," J. Comput Chem, 10(8):982-1012.
Collino et al., (2006) "Modulation of the Oxidative Stress and Inflammatory Response by PPAR-gamma Agonists in the Hippocampus of Rats Exposed to Cerebral Ischemia/Reperfusion," Eur J Pharmacol, 530(1-2):70-80.
Corse et al., (1948) "Biosynthesis of Penicillins" J Am Chem Soc, 70(9):2837-43.
Database CA [Online] Chemical Abstracts Service, Columbus Ohio, US; Database Accession No. 67.50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Database Accession No. 107:235800, Abstract of Cleary, et al., "Methylenecyclopropane rearrangement as a probe for free radical substituent effects.. sigma.. bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).
Database CA [Online] Chemical Abstracts Service, Columbus, Ohio, US, Database Accession No. 131:144358, Abstract of Lamy-

(56) References Cited

OTHER PUBLICATIONS

Pitara, et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Accession No. 2010:351508, Abstract of Baroni, et al., "Compounds for the selective treatment of intestinal immuninflammatory component of the celiac disease", (2007).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-)(alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49.68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database CA Registry [Online] Chemical Abstracts Service, Columbus, Ohio, US; Database Accession No. 1001756-73-5, Abstract & "Allichem Catalog" Jun. 3, 2009; XP002595814, (2008).
Database Caplus Chemical Abstracts Service, Columbus, Ohio, US; Database Accession No. 1913:10241, Abstract of Heller: Berichte der Deutschen Chemischen Gesellschaft (1913), 46:280-294.
Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of $(--)$-β-hydroxy-β-(m-hydroxyphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 2, 2008.
Delbarre et al., (1964), "Chemical Abstracts, vol. 65, Columbus , Ohio, Abstract No. 93711, Non-steroid Antiinflammatory Substances. I. Derivatives of the 4- and 5-Aminosalicylic Acids," Med Exp Int J Exp Med, 11:389-96.
Deljac et al., (1967) "Absolute Configuration of $(-)$-β-Hydroxy-β-(m)-Hydroxyphenyl)-Propionic Acid," Recueil des Travaux Chimiques des Pays-Bas, 86:765-8.
Dimon-Gadal et al., (2000) 'Increased Oxidative Damage to Fibroblasts in Skin With and Without Lesions in Psoriasis,' J Invest Dermatol,114(5):984-9.
Ding, et al, (2012) "Mucosal Healing and Fibrosis after Acute or Chronic Inflammation in Wild Type FVB-N Mice and C57BL6 Procollagen α1 (I)-Promoter-GFP Reporter Mice",PLoS ONE, vol. 7, No. 8, p. e42568, XP055433727.
DiPoï et al., (2004) 'Functions of Peroxisome Proliferator-Activated Receptors (PPAR) in Skin Homeostasis,' Lipids, 39(11):1093-9.
DiPoï et al., (2005) 'Epithelium-Mesenchyme Interactions Control the Activity of Peroxisome Proliferator-Activated Receptor β/δ During Hair Follicle Development,' Mol Cell Biol, 25(5):1696-1712 (2005).
Doshi et al., (1997) "A Comparison of Current Acne Grading Systems and Proposal of a Novel System," Int J Dermatol, 36(6):416-8.
Drosner M et al., (2005), 'Photo-Epilation: Guidelines for Care from the European Society for Laser Dermatology (ESLD),' J Cosmet Laser Ther, 7(1):33-8.
Dubuquoy et al., (2002) "Role of peroxisome proliferator-activated receptor γ and retinoid X receptor heterodimer in hepatogastroenterological diseases," Lancet, 360(9343):1410-8.
Dubuquoy et al., (2003) "Impaired Expression of Peroxisome Proliferator-Activated Receptor Gamma in Ulcerative Colitis," Gastroenterology, 124(5):1265-76.
Dyall-Smith, D, "Lichen Planopilaris," , 2011, pp. 1-4 [online] [retrieved on Mar. 29, 2018] Retrieved from http://www.dermnetnz.org/topics/lichen-planopilaris.
Egan et al., (2003) "Clinical Pharmacology in Inflammatory Bowel Disease: Optimizing Current Medical Therapy," *Inflammatory Bowel Disease: From Bench to Bedside, ($2^{nd}$ Ed, 2003)*, Stephan R Targan et al. (Eds), Springer Publishingm New York, NY (Publ), pp. 495-521.
Ellis et al., (2007) "Placebo Response in Two Long-Term Randomized Psoriasis Studies that were Negative for Rosiglitazone," Am J Clin Dematol, 8(2):93-102.
European Clinical Trials Register, (2012), entry EudraCT No. 2011-003283-78 [online] Mar. 1 2012, [retrieved from the internet at <https://www.clinicaltrialsregister.eu/ctr-search/trial/2011-003283-78/IT> on Feb. 1, 2017] European Union Clinical Trials Register, XO-002766683 (6 pages).
Examination Report dated Apr. 15, 2011 for Application No. 06 766 083.7-2103 (11 pages).

(56) References Cited

OTHER PUBLICATIONS

Fernholz et al., (1992) "Specificity of Antibody-Catalyzed Transesterifications Using Enol Esters: A Comparison with Lipase Reactions," J Org Chem, 57(17):4756-61.
Floch and White, (2006), 'Management of Diverticular Disease is Changing,' World J Gastroenterol, 12(20):3225-8.
Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J Biol Chem, 282(51):37006-15.
Gampe et al., (2000) "Asymmetry in the PPARγ/RXRα Crystal Structure Reveals the Molecular Basis of Heterodimerization Among Nuclear Receptors," Mol Cell, 5(3):545-55.
Garza LA et al., (2011), 'Bald Scalp in Men with Androgenetic Alopecia Retains Hair Follicle Stem Cells but Lacks CD200-Rich and CD34-Positive Hair Follicle Progenitor Cells,' J Clin Invest, 121(2):613-22.
Gerdes et al., (1986) "Growth Fractions in Breast Cancers Determined in Situ with Monoclonal Antibody Ki-67," J Clin Pathol, 39(9):977-80.
GlaxoSmithKline. (2008) Scientific Result Summary for Clinical Study ID 49653/292. "A Randomized, Double-Blind, Placebo-Controlled Trial to Assess Three Dose Levels of Rosiglitazone Maleate in the Treatment of Moderate to Severe Plaque Psoriasis," [retrieved from <https://www.gsk-clinicalstudyregister.com/study/49653/292> on Jul. 25, 2017] (3 pages).
Gormin (1989), "Picosecond Transient Absorption Spectra of Aminosalicylates in Confirmation of the Triple Excitation Mechanism," J Phys Chem, 93(16):5979-80.
Guo et al., (2009) "Effect of Uyghur Compound Xipayi Kui Jie' an on the Ultrastructure of Small Intestinal Epithelial Cell in Rat Model of Ulcerative Colitis," J Xinjiang Medi Univ, 32(7):893-4.
Haemmerli U P et al (1965) "Acquired milk intolerance in the adult caused by lactose malabsorption due to a selective deficiency of intestinal lactase activity," American Journal of Medicine, vol. 38, pp. 7-30.
Harari (2004) "Epidermal Growth Factor Receptor Inhibition Strategies in Oncology," Endocr Relat Cancer, 11(4):689-708.
Harrington et al., (2008) 'A Re-appraisal of Lactose Intolerance,' Int J Clin Pract, 62(10):1541-6.
Husova et al., (2007) "Hepatopathy, Coeliac Disease and Lymphocytic Colitis," Ceska A. Slovenska Gastroenterologie A. Hepatologie—CZ SL Gastroenterol Hepatol, 61(6):309-13.
International Preliminary Report on Patentability and Written Opinion of the International Searching Authority for PCT/IE2006/000076, dated Jan. 22, 2008 (10 pages).
International Preliminary Report on Patentability and Written Opinion of the International Searching Authority for PCT/EP13/057729, dated Oct. 21, 2014 (6 pages).
International Preliminary Report on Patentability and Written Opinion of the International Searching Authority for PCT/EP2009/008631, dated Jun. 7, 2011(13 pages).
International Preliminary Report on Patentability and Written Opinion of the International Searching Authority for PCT/EP2009/008633, dated Jun. 7, 2011 (6 pages).
International Preliminary Report on Patentability and Written Opinion of the International Searching Authority for PCT/EP2010/000935, dated Aug. 16, 2011 (7 pages).
International Preliminary Report on Patentability and Written Opinion of the International Searching Authority for PCT/EP2010/000939, dated Aug. 16, 2011 (8 pages).
International Preliminary Report on Patentability and Written Opinion of the International Searching Authority for PCT/EP2013/052617, dated Aug. 12, 2014 (5 pages).
International Preliminary Report on Patentability and Written Opinion of the International Searching Authority for PCT/EP2013/069062, dated Mar. 17, 2015 (7 pages).
International Preliminary Report on Patentability and Written Opinion of the International Searching Authority for PCT/EP2013/069063, dated Mar. 17, 2015 (7 pages).
International Preliminary Report on Patentability and Written Opinion of the International Searching Authority for PCT/IE2006/000078, dated Jan. 22, 2008 (14 pages).
International Preliminary Report on Patentability for PCT/EP2008/052354, completed May 22, 2009 (20 pages).
International Preliminary Report on Patentability for PCT/EP2008/068265, completed Apr. 12, 2010 (11 pages).
International Search Report and Written Opinion of the International Search Authority for International Application No. PCT/EP2016/071995—dated Jan. 16, 2017 (21 pages total).
International Search Report and Written Opinion of the International Search Authority for International Application No. PCT/EP2017/054526—dated Feb. 6, 2017 (20 pages total).
International Search Report and Written Opinion of the International Searching Authority for International Application No. PCT/EP2016/079512 dated Feb. 28, 2017 (15 pages).
International Search Report and Written Opinion of the International Searching Authority for PCT/IE2006/000078, dated Jan. 26, 2007 (14 pages).
International Search Report for PCT/EP2008/052354, dated Jun. 9, 2008 (6 pages).
International Search Report for PCT/EP2008/068265, dated Aug. 11, 2009 (5 pages).
International Search Report for PCT/EP2009/008631, dated Aug. 19, 2010 (9 pages).
International Search Report for PCT/EP2009/008633, dated Feb. 22, 2010 (4 pages).
International Search Report for PCT/EP2010/000935 dated Aug. 23, 2010 (5 pages).
International Search Report for PCT/EP2010/000939 dated Sep. 20, 2010 (5 pages).
International Search Report for PCT/EP2013/052617, dated Aug. 12, 2014 (4 pages).
International Search Report for PCT/EP2013/057729, dated Jun. 11, 2013 (4 pages).
International Search Report for PCT/EP2013/069062, dated Dec. 10, 2013 (3 pages).
International Search Report for PCT/EP2013/069063, dated Dec. 20, 2013 (3 pages).
International Search Report for PCT/IE2006/000076, dated Feb. 1, 2007 (5 pages).
Ireland et al., (1992) "Comparison of 5-Aminosalicylic Acid and N-Acetylaminosalicylic Acid Uptake by the Isolated Human Colonic Epithelial Cell," Gut, 33(10):1343-7.
Janda et al., (1988) "Antibody Catalysis of Bimolecular Amide Formation," J Am Chem Soc, 110(14):4835-7.
Jiang J et al (1997) "Conjugated Linoleic Acid in Swedish dairy products with special reference to the manufacture of hard cheeses," International Dairy Journal, vol. 7, No. 12, pp. 863-867.
Johnson et al., (2012) 'Intestinal Fibrosis Is Reduced by Early Elimination of Inflammation in a Mouse Model of IBD: Impact of a "Top-Down" Approach to Intestinal Fibrosis in Mice,' Inflamm Bowel Dis, 18(3):460-71.
Jones et al., (1997) "Development and Validation of a Genetic Algorithm for Flexible Docking," J Mol Biol, 267(3):727-48.
Julien et al., (2005) 'Antifibrogenic Role of the Cannabinoid Receptor CB2 in the Liver,' Gastroenterology, 128(3):742-55.
Kari et al., (2003) "Targeting the Epidermal Growth Factor Receptor in Cancer: Apoptosis Takes Center Stage," Cancer Res, 63(1):1-5.
Karnik et al., (2009) 'Hair Follicle Stem Cell-specific PPARy Deletion Causes Scarring Alopecia,' J Invest Dermatol, 129(5):1243-57.
Kloepper et al., (2008) 'Immunophenotyping of the Human Bulge Region: The Quest to Define Useful in situ Markers for Human Epithelial Hair Follicle Stem Cells and their Niche,' Exp Dermatol, 17(7):592-609.
Koeffler, (2003), "Peroxisome Proliferator-activated Receptor γ and Cancers," Clin Cancer Res, 9(1):1-9.
Kuenzli and Saurat, (2003) 'Effect of Topical PPARβ/δ and PPARγ Agonists on Plaque Psoriasis: A Pilot Study,' Dermatology, 206(3):252-6.

(56) References Cited

OTHER PUBLICATIONS

Lavker RM et al., (2003), 'Hair Follicle Stem Cells,' J Investig Dermatol Symp Proc, 8(1):28-38.
Lees et al., (2008) 'Analysis of Germline GLI1 Variation Implicates Hedgehog Signalling in the Regulation of Intestinal Inflammatory Pathways,' PLoS Med, 5(12):e239 (15 pages).
Li L and Xie T, (2005), 'Stem Cell Niche: Structure and Function,' Annu Rev Cell Dev Biol, 21:605-31.
Liao et al., (1990) 'Therapeutic Effect of Methyl 5-Aminosalicylate on Experimental Ulcerative Colitis in Rabbits,' Acta Pharmacologica Sinica 11(1):54-6.
Lin et al., (1998) "An Antibody Transesterase Derived from Reactive Immunization that Utilizes a Wide Variety of Alcohol Substrates," Chem Commun, 10:1075-6.
Lowe, D. (2009) "More Binding Site Weirdness," CORANTE: In the Pipeline, pp. 1-4.
Lukovac S et al (2008) "Essential Fatty Acid (EFA) Deficiency in Mice Impairs Lactose Digestion", Abstract M1730, Annual Meeting of the American Gastroenterological Association (AGA) Institute and Digestive Disease Week, May 17-22, 2008, San Diego, CA, Gastroenterology, vol. 134, No. 4, Supplement 1, pp. A-406-A407.
Mager et al., (1979) "Struktur-Wirkungs-Beziehungen bei Salizylsaure- und Benzoesaurederivaten," Zbl. Pharm. 118(Heft 12):1259-75 (concise explanation of relevance attached).
Mandt N et al., (2005), 'Epilation Today: Physiology of the Hair Follicle and Clinical Photo-Epilation,' J Investig Dermatol Symp Proc, 10(3):271-4.
Mangelsdorf et al., (1995) "The Nuclear Receptor Superfamily: The Second Decade," Cell, 83(6): 835-9.
Medline Database, (2013), U.S. National Library of Medicine, Bethesda, MD, XP002763389, Accession No. NLM23651165, Benjamin B et al., 'PPAR-gamma in Ulcerative Colitis: A Novel Target for Intervention,' Curr Drug Targ, 14(12):1501-7.
Medow et al., (1990) 'β-Galactosidase Tablets in the Treatment of Lactose Intolerance in Pediatrics,' Am J Dis Child, 144(11):1261-4 (Abstract).
Meek et al., (1969) "Carboxylation of Substituted Phenols in N,N-Dimethylamide Solvents at Atmospheric Pressure," J Chem Eng Data, 14(3):388-91.
Melgar, et al (2005) "Acute colitis induced by dextran sulfate sodium progresses to chronicity in C57BL6 but not in BALB/c mice: correlation between symptoms and inflammation", American Journal of Physiology—Gastrointestinal and Liver Physiology, vol. 288, No. 6, pp. G1328-G1338, XP055433729.
Mendelsohn (2001) "The Epidermal Growth Factor Receptor as a Target for Cancer Therapy," Endocr Relat Cancer, 8(1):3-9.
Merck Manual Home Edition, "Ulcerative Colitis", Merck Sharp & Dohme Corp., Copyright © 2004-2011, pp. 1-6 [online] [retrieved on Apr. 19, 2013] Retrieved from http://www.merckmanuals.com/home/print/digestive_disorders/inflammatory_bowel_diseases_ibd/ulcerative_colitis.html.
Michalik and Wahli, (2007) 'Peroxisome Proliferator-activated Receptors (PPARs) in Skin Health, Repair and Disease,' Biochim Biophys Acta, 1771(8):991-8.
Mirmirani and Karnik, (2009), 'Lichen Planopilaris Treated with a Peroxisome Proliferator-Activated Receptor γ Agonist,' Arch Dermatol, 145(12):1363-6 [NIH Public Access Author Manuscript].
Misra et al., (2002) "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J Biol Chem, 277(50): 48745-54.
Nolte et al., (1998) "Ligand Binding and Co-Activator Assembly of the Peroxisome Proliferator-Activated Receptor-γ," Nature, 395(6698):137-43.
O'Mahony, et al., (1990) "Coeliac Disease and Collagenous Colitis," Postgrad Med, 66(773):238-41.
Office Action issued in Japanese Patent Application No. 2011-549494 dated Feb. 25, 2014, with English language translation (8 pages).

Osawa et al., (2003) "Peroxisome Proliferator-Activated Receptor γ Ligands Suppress Colon Carcinogenesis Induced by Azoxymethane in Mice," Gastroenterology, 124(2):361-7.
Oshima H et al., (2001), 'Morphogenesis and Renewal of Hair Follicles from Adult Multipotent Stem Cells,' Cell, 104(2):233-45.
Pedersen et al., (2010) 'Topical Rosiglitazone Treatment Improves Ulcerative Colitis by Restoring Peroxisome Proliferator-Activated Receptor-γ Activity,' Am J Gastroenterol, 105(7):1596-1603 (Abstract).
Pershadsingh et al., (2005) 'Improvement in Psoriasis with Rosiglitazone in a Diabetic and a Nondiabetic Patient,' Skinmed, 4(6):386-90 (Abstract).
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Peyrin-Biroulet, et al. (2007) "Peroxisome Proliferator-Activated Receptor Gamma Functions as an Antibacterial Factor," J Crohns Colitis Suppl, 1(1):2.
Ponchant et al., (1991) Synthesis of 5-[$^{125}$I]-Iodo-Zacopride, a New Probe for 5-HT$_3$ Receptor Binding Sites, Journal of Labelled Compounds and Radiopharmaceuticals, 29(10):1147-55.
Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-peptidomimetic Using Multivesicular Liposomes Lowers Serum Cholesterol Levels,' J Control Release, 79(1-3):207-18.
Rathi, (2011), 'Acne Vulgaris Treatment: The Current Scenario,' Indian J Dermatol, 56(1):7-13.
Reifen, Ram, et al. (2004) "5-ASA and Lycopene Decrease the Oxidative Stress and Inflammation Induced by Iron in Rats with Colitis," J Gastroenterol, 3996):514-9.
Result Summary for Study ID No. SB-999910/150 (2002) "A Study in Patients with Crohn's Disease to Evaluate the Effect of AVANDIA™ on Inflammatory Activity Mediated by Monocytes/Macrophages" Retrieved from: download.gsk-clinicalstudyregister.com/files/23093.pdf on May 23, 2012 (2 pages).
Risérus et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes, 57(NR. 2):332-9.
Ritland et al., (1999) 'Evaluation of 5-Aminosalicylic Acid (5-ASA) for Cancer Chemoprevention: Lack of Efficacy against Nascent Adenomatous Polyps in the Apc$^{Min}$ Mouse,' Clin Cancer Res, 5(4):855-63.
Robertson et al., (1985) 'Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine,' J Med Chem, 28(6):717-27.
Rousseaux et al., (2005) "Intestinal Anti-inflammatory Effect of 5-Aminosalicylic Acid is Dependent on Peroxisome Proliferator-Activated Receptor-γ," J Exp Med, 201(8):1205-15.
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5-Suppl 1):S-157.
Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515(Abstract).
Rovner (2009) "An Enzyme Reveals an Unexpected Inclusiveness, Protein Binding: Bacterial Enzyme's Active Site Welcomes Both Enantiomers of a Chiral Molecule at the Same Time," Chem Eng News, Nov. 5, 2009 issue, (2 pages) retrieved from http://cen.acs.org/articles/87/web/2009/11/Enzyme-Reveals-Unexpected-Inclusiveness.html?type-paidArticleContent.
Schauber J et al., (2004) 'Histone-Deacetylase Inhibitors Induce the Cathelicidin LL-37 in Gastrointestinal Cells,' Mol Immunol, 41(9):847-54.

(56) References Cited

OTHER PUBLICATIONS

Schwab et al., (2007) 'Role of Nuclear Hormone Receptors in Butyrate-Mediated Up-Regulation of the Antimicrobial Peptide Cathelicidin in Epithelial Colorectal Cells,' Mol Immunol, 44(8):2107-14.
Sherwin (1924), "Acetylation as a Physiologic Reaction," Proc Soc Exper Biol & Med, 22:182.
Speca et al., (2012) 'Cellular and Molecular Mechanisms of Intestinal Fibrosis,' World J Gastroenterol, 18(28):3635-61.
Tanaka et al.,(2001) "Ligands for Peroxisome Proliferator-Activated Receptors α and γ Inhibit Chemically Induced Colitis and Formation of Aberrant Crypt Foci in Rats," Cancer Res., 61(6): 2424-8.
Tosti et al., (2009) 'Treatment Strategies for Alopecia,' Expert Opin Pharmacother, 10(6):1017-26.
Troilius A and Troilius C, (1999), 'Hair Removal with a Second Generation Broad Spectrum Intense Pulsed Light Source—A Long Term Follow-up,' J Cutan Laser Ther, 1(3):173-8.
Tuleu, et al., (2002) "Colonic Delivery of 4-Aminosalicylic Acid Using Amylose-Ethyl Cellulose-Coated Hydroxypropyl Methyl Cellulose Capsules," Aliment Pharmacol Ther., 167(10):1771-9.
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.
Tursi, (2004), 'Acute Diverticulitis of the Colon—Current Medical Therapeutic Management,' Exp Opin Pharmacother, 5(1):55-9.
Tzameli et al., (2004) 'Regulated Production of a Peroxisome Proliferator-Activated Receptor-γ Ligand During an Early Phase of Adipocyte Differentiation in 3T3-L1 Adipocytes,' J Biol Chem, 279(34):36093-102.
Van't Riet, Bart, et al. (1979) "Synthesis of Hydroxy and Amino-Substituted Benzohydroxamic Acids: Inhibition of Ribonucleotide Reductase and Antitumor Activity," J Med Chem, 22(5) 589-92.
Venkatraman et al., (2004) 'Alpha-Lipoic Acid-Based PPARγ Agonists for Treating Inflammatory Skin Diseases,' Arch Dermatol Res, 296(3):97-104 (Abstract).
Wallace et al., (1989) 'Inhibition of Leukotriene Synthesis Markedly Accelerates Healing in Rat Model of Inflammatory Bowel Disease,' Gastroenterology, 96(1):29-36.
Wang et al., (2002) "Further Development and Validation of Emphirical Scoring Functions for Structure-Based Binding Affinity Prediction," J Comput Aided Mol Des, 16(1):11-26.
Wang et al., (2004) 'Cutting Edge: 1,25-Dihydroxyvitamin D3 is a Direct Inducer of Antimicrobial Peptide Gene Expression,' J Immunol, 173(5):2909-12.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Westin et al., (1998) "Interactions Controlling the Assembly of Nuclear-Receptor Heterodimers and Co-Activators," Nature, 395(6698):199-202.
Williams and Hallett (1989) "Effect of Sulphasalazine and its Active Metabolite, 5-Amino-Salicylic Acid, on Toxic Oxyden Metabolite Production by Neutrophils," Gut, 30(11):1581-7.
Written Opinion of the International Searching Authority for International Application No. PCT/EP2008/052354 dated Jun. 9, 2008 (10 pages).
Written Opinion of the International Searching Authority for International Application No. PCT/EP2008/068265 dated Aug. 11, 2009 (12 pages).
Written Opinion of the International Searching Authority for International Application No. PCT/IE2006/000076 dated Feb. 1, 2007 (9 pages).
Wu et al., (2006) 'Effects of Rosiglitazone on Expression of TGF-A1 in Experimental Hepatic Fibrosis Rats,' Chin J Gastroenterol Hepatol, 15(2):126-9.
Xu et al., (2001) "Structural Determinants of Ligand Binding Selectivity Between the Peroxisome Proliferator-Activated Receptors," Proc Natl Acad Sci USA, 98(24):13919-24.
Yanai et al., (2004) "Para-Position Derivatives of Fungal Anthelmintic Cyclodepsipeptides Engineered with Streptomyces Venezuelae Antibiotic Biosynthetic Genes," Nat Biotechnol, 22(7):848-55.
Ye; "Regulation of PPARy function by TNF-a"; 2008; Biochemical and Biophysical Research Communications; 374: 405-408 (Year: 2008).
Youssef and Badr, (2004) "Role of Peroxisome Proliferator-Activated Receptors in Inflammation Control," J Biomed Biotechnol, 2004(3):156-66.
Yu et al., (2010) 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, 42(6):948-57.
Zhou et al., (1999) 'Intestinal Metabolism and Transport of 5-Aminosalicylate,' Drug Metab Dispos, 27(4):479-85.
U.S. Appl. No. 13/131,978, Methods for Preventing or Reducing Colon Carcinogenesis, fiiled Aug. 11, 2011, Abandoned.
U.S. Appl. No. 15/088,654, Methods for Preventing or Reducing Colon Carcinogenesis, filed Apr. 1, 2016, Patented U.S. Pat. No. 9,913,817.
U.S. Appl. No. 15/884,864, Methods for Preventing or Reducing Colon Carcinogenesis, filed Jan. 31, 2018, Abandoned.
U.S. Appl. No. 13/201,786, Alkylamido Compounds and Uses Thereof, filed Nov. 17, 2011, Patented U.S. Pat. No. 8,754,127.
U.S. Appl. No. 14/255,255, Alkylamido Compounds and Uses Thereof, filed Apr. 17, 2014, Patented U.S. Pat. No. 9,511,041.
U.S. Appl. No. 15/337,707, Alkylamido Compounds and Uses Thereof, filed Oct. 28, 2016, Patented U.S. Pat. No. 10,137,101.
U.S. Appl. No. 16/149,524, Alkylamido Compounds and Uses Thereof, filed Oct. 2, 2018, Pending.
U.S. Appl. No. 13/131,982, Methods of Preventing or Reducing Colon Carcinogenesis, filed Aug. 11, 2011, Patented U.S. Pat. No. 8,501,806, Abandoned.
U.S. Appl. No. 12/528,522, PPAR-Gamma Agonists for the Induction of Cationic Antimicrobial Peptide Expression as Immunoprotective Stimulants, filed Mar. 4, 2011, Published US 2011/0152225 Abandoned.
U.S. Appl. No. 13/201,790, Methods of Treating Hair Related Conditions, filed Nov. 17, 2011, Patented U.S. Pat. No. 8,796,334.
U.S. Appl. No. 14/314,738, Methods of Treating Hair Related Conditions, filed Jun. 25, 2014, Abandoned.
U.S. Appl. No. 14/969,939, Methods of Treating Hair Related Conditions, filed Dec. 15, 2015, Patented U.S. Pat. No. 9,901,557.
U.S. Appl. No. 11/989,090, Compounds and Their Salts Specific to the PPAR Receptors and the EGF Receptors and Their Use in the Medical Field, filed Jun. 6, 2008, Patented U.S. Pat. No. 8,153,841.
U.S. Appl. No. 13/408,439, Compounds and Their Salts Specific to the PPAR Receptors and the EGF Receptors and Their Use in the Medical Field, filed Feb. 29, 2012, Patented U.S. Pat. No. 8,710,100.
U.S. Appl. No. 14/202,386, Compounds and Their Salts Specific to the PPAR Receptors and the EGF Receptors and Their Use in the Medical Field, filed Mar. 10, 2014, Patented U.S. Pat. No. 9,133,099.
U.S. Appl. No. 14/671,579, Compounds and Their Salts Specific to the PPAR Receptors and the EGF Receptors and Their Use in the Medical Field, filed Mar. 27, 2015, Patented U.S. Pat. No. 9,561,202.
U.S. Appl. No. 15/377,013, Compounds and Their Salts Specific to the PPAR Receptors and the EGF Receptors and Their Use in the edical Field, filed Dec. 13, 2016, Patented U.S. Pat. No. 10,016,381.
U.S. Appl. No. 14/671,585, Compounds and Their Salts Specific to the PPAR Receptors and the EGF Receptors and Their Use in the Medical Field, filed Mar. 27, 2015, Patented U.S. Pat. No. 9,345,680.
U.S. Appl. No. 11/989,033, Compounds and Their Salts Specific to the PPAR Receptors and EGF Receptors and Their Use in the Medical Field, filed Jun. 6, 2008, Patented U.S. Pat. No. 8,138,357.
U.S. Appl. No. 13/397,245, Compounds and Their Salts Specific to the PPAR Receptors and EGF Receptors and Their Use in the Medical Field, filed Feb. 15, 2012, Patented U.S. Pat. No. 8,450,506.
U.S. Appl. No. 13/785,485, Compounds and Their Salts Specific to the PPAR Receptors and EGF Receptors and Their Use in the Medical Field, filed Mar. 5, 2013, Abandoned.

(56) References Cited

OTHER PUBLICATIONS

U.S. Appl. No. 12/810,159, Compounds for the Selective Treatment of the Intestinal Immuno-Inflammatory Component of the Celiac Disease, filed Aug. 16, 2010, Patented U.S. Pat. No. 8,153,693.
U.S. Appl. No. 13/331,173, Compounds for the Selective Treatment of the Intestinal Immuno-Inflammatory Component of the Celiac Disease, filed Dec. 20, 2011, Abandoned.
U.S. Appl. No. 14/377,362, Methods of Treating Fibrosis, filed Aug. 7, 2014, Patented U.S. Pat. No. 9,682,923.
U.S. Appl. No. 15/593,864, Methods of Treating Fibrosis, filed May 12, 2017, Published US 2018/0065921.
U.S. Appl. No. 14/394,916, Methods of Treating Lactose Intolerance, filed Oct. 16, 2014, Patented U.S. Pat. No. 9,682,050.
U.S. Appl. No. 15/594,023, Methods of Treating Lactose Intolerance, filed May 12, 2017, Abandoned.
U.S. Appl. No. 14/428,048, Methods of Inhibiting Hair Growth, filed Mar. 13, 2015, Abandoned.
U.S. Appl. No. 14/428,164, Methods of Treating Hair Related Conditions, filed Mar 13, 2015, Published US 2015/0250749.

\* cited by examiner

METHODS OF TREATING HAIR RELATED CONDITIONS

RELATED APPLICATIONS

This application is a continuation of U.S. application Ser. No. 14/969,939, filed Dec. 15, 2015, which is a continuation of U.S. application Ser. No. 14/314,738, filed Jun. 25, 2014, which is a continuation of U.S. application Ser. No. 13/201,790, filed Nov. 17, 2011, which is a national stage filing under 35 U.S.C. 371 of PCT/EP2010/000939, filed Feb. 16, 2010, which claims priority to EP09425056.0, filed Feb. 16, 2009; U.S. Ser. No. 61/179,062, filed May 18, 2009; and U.S. Ser. No. 61/287,461, filed Dec. 17, 2009, the entire disclosures of each of which are incorporated by reference in their entirety.

BACKGROUND

Peroxisome Proliferator Activated Receptors (PPARs) are members of the nuclear hormone receptor super family, which are ligand-activated transcription factors regulating gene expression. Certain PPARs play roles in the regulation of cell differentiation, development and metabolism of higher organisms.

Three types of PPAR has been identified: alpha, expressed in the liver, kidney, heart and other tissues and organs, beta/delta expressed for example in the brain, and gamma, expressed in three forms: gamma1, gamma2, and gamma3. PPARγ receptors have been associated with stimulation of keratinocyte differentiation, and has served as a potential drug target for a number of disease states including skin disorders such as psoriasis and atopic dermatitis. Further, PPAR expression has been shown in hair follicles, and may be involved in hair growth.

Hair loss is a common problem, which can be the result of illness, functional disorder, or hereditary disposition. In some cases, hair loss can be localized on the body (e.g. male pattern baldness), or can occur body-wide. Alcopecia is a medical term for the absence or loss of hair, and can occur in patients undergoing treatment for cancer or for other diseases that require treatment with cytotoxic drugs.

De-pigmentation of hair is also a common problem, and is typically a result of the aging process. At some point in the aging process, stem cells at the base of hair follicles responsible for producing melancytes (cells that produce and store pigment) produce less pigment, until the hair has little pigment.

Accordingly, effective agents, such as PPAR modulators, that are useful in the treatment of such hair disorders are needed.

SUMMARY

This disclosure is generally directed methods of treating, ameliorating or substantially preventing hair related disorders or conditions, for example, provided herein is a method for treating or ameliorating a hair related condition in a subject in need thereof, comprising administering an effective amount to the subject of a composition comprising a compound represented by Formula I:

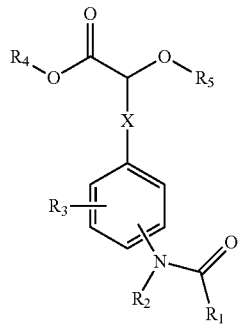

wherein X is $C_1$-$C_3$alkylene (e.g., $(CH_2)_n$, wherein n is 1 or 2), optionally substituted with one, two or three substituents selected from halogen or hydroxyl;

$R_1$ is selected from the group consisting of $C_1$-$C_6$alkyl, $C_3$-$C_6$cycloalkyl, $C_2$-$C_6$alkenyl, and $C_2$-$C_6$alkynyl (for example, $R_1$ may be methyl);

$R_2$ is selected from the group consisting of hydrogen and $C_1$-$C_6$alkyl;

$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_4$ is selected from the group consisting of hydrogen and $C_1$-$C_6$alkyl;

$R_5$ is hydrogen or $C_1$-$C_6$alkyl (e.g., ethyl or methyl); or pharmaceutically acceptable salts or N-oxides thereof; wherein the composition optionally further comprises an carrier. An exemplary compound is N-acetyl-(R)-(−)-3-(4-aminophenyl)-2-methoxypropionic acid.

For example, methods of treating or ameliorating hair related conditions are provided herein, such as hair depigmentation, limited or short hair growth, hair loss, vitiligo, or alopecia (e.g., anagen alopecia, telogen alopecia, or alopecia areata.

A method of stimulating hair growth is also provided comprising administering to a subject in need thereof an effective amount of a composition (e.g. a pharmaceutically and/or cosmetically acceptable composition) comprising a compound disclosed herein, such as those represented by Formula I, above. Such compositions may be for example administered topically. wherein the composition is pharmaceutically or cosmetically acceptable. In some embodiments, disclosed composition may further comprise an hair stimulating agent.

Also contemplated herein are compositions that include a compound represented by formula I or II and e.g., a pharmaceutically acceptable excipient.

Also provided are compounds represented by formulas I and II for use in therapy and/or for the manufacture of a medicament for the treatment or ameliorate of hair loss or hair-depigmentation.

DETAILED DESCRIPTION

Figure 1:
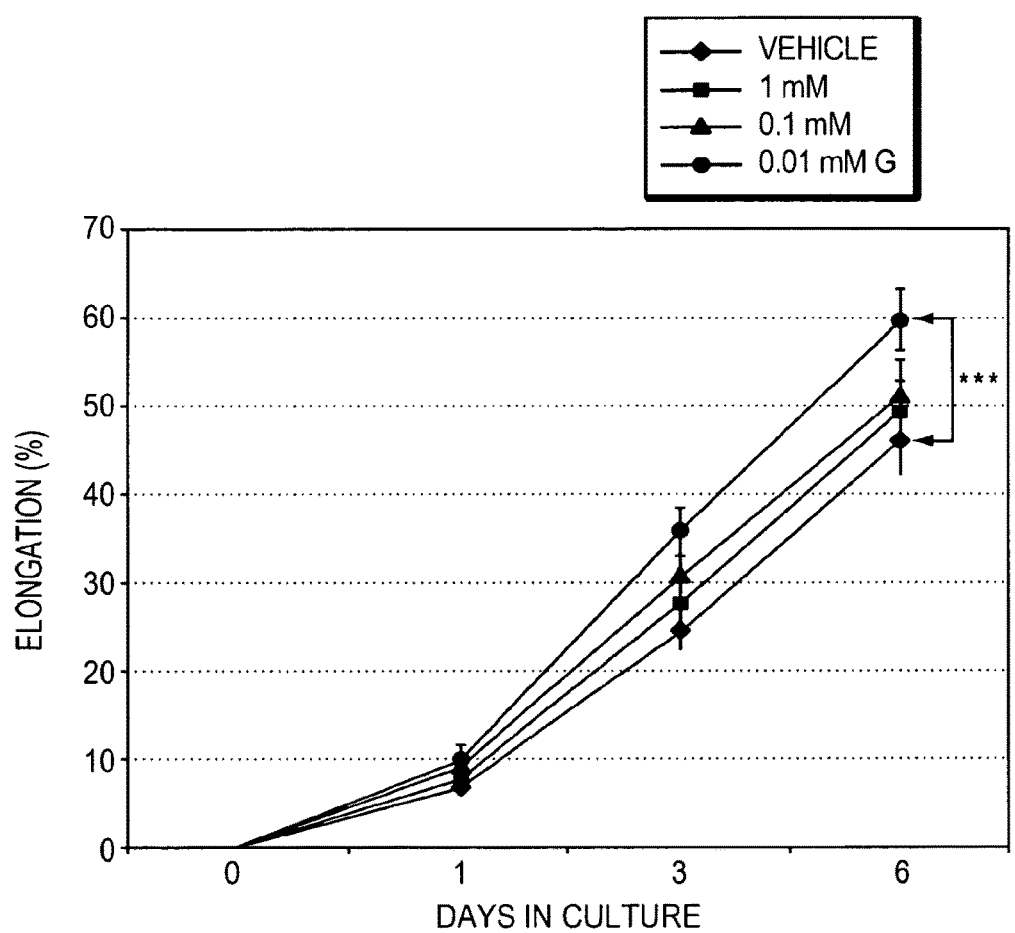
FIG. 1 depicts stimulation of hair shaft elongation for various concentrations of N-acetyl E2.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to, groups with an alkyl, alkenyl or alkynyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. In certain embodiments, alkyl refers to $C_1$-$C_6$ alkyl. In certain embodiments, cycloalkyl refers to $C_3$-$C_6$cycloalkyl.

Alkyl, alkenyl and alkynyl groups can, in some embodiments, be optionally be substituted with or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —$R_a$C(O)N($R_b$)—, —$R_a$C(O)N($R_b$) $R_c$—, or —C(O)N$R_b R_c$, wherein $R_a$, $R_b$ and $R_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —C(O)N$R_b R_c$.

The term "amidino" as used herein refers to a radical of the form —C(=NR)NR'R" where R, R', and R" can each independently be selected from alkyl, alkenyl, alkynyl, amide, aryl, arylalkyl, cyano, cycloalkyl, haloalkyl, heteroaryl, heterocyclyl, hydroxyl, ketone and nitro.

The term "amine" or "amino" as used herein refers to a radical of the form —N$R_d R_e$, —N($R_d$)$R_e$—, or —$R_e$N($R_d$) $R_f$— where $R_d$, $R_e$, and $R_f$ are independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amino can be attached to the parent molecular group through the nitrogen, $R_d$, $R_e$ or $R_f$. The amino also may be cyclic, for example any two of Rd, Re or Rf may be joined together or with the N to form a 3- to 12-membered ring, e.g., morpholino or piperidinyl. The term amino also includes the corresponding quaternary ammonium salt of any amino group, e.g., —[N(Rd)(Re)(Rf)]+. Exemplary amino groups include aminoalkyl groups, wherein at least one of $R_d$, $R_e$, or $R_f$ is an alkyl group.

The term "aryl" as used herein refers to refers to a mono-, bi-, or other multi-carbocyclic, aromatic ring system. In certain embodiments, aryl refers to a monocyclic and/or bicyclic, 5 to 6 membered ring. The aromatic ring may be substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms. For example, "phenylalkyl" includes phenylC$_4$alkyl, benzyl, 1-phenylethyl, 2-phenylethyl, etc.

The term "carbonyl" as used herein refers to the radical —C(O)—.

The term "carboxamido" as used herein refers to the radical —C(O)NRR', where R and R' may be the same or different. R and R' may be selected from, for example, alkyl, aryl, arylalkyl, cycloalkyl, formyl, haloalkyl, heteroaryl and heterocyclyl.

The term "carboxy" as used herein refers to the radical —COOH or its corresponding salts, e.g. —COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12, 3-8, 4-8, or 4-6 carbons, referred to herein, e.g., as "C$_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Cycloalkyl groups may be substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, cycloalkyl refers to C$_3$-C$_6$ alkyl.

The terms "halo" or "halogen" or "Hal" as used herein refer to F, Cl, Br, or I.

The term "haloalkyl" as used herein refers to an alkyl group substituted with one or more halogen atoms.

The term "nitro" as used herein refers to the radical —NO$_2$.

The term "phenyl" as used herein refers to a 6-membered carbocyclic aromatic ring. The phenyl group can also be fused to a cyclohexane or cyclopentane ring. Phenyl can be substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "phosphate" as used herein refers to the radical —OP(O)(OR$_{aa}$)$_2$ or its anions. The term "phosphanate" refers to the radical —P(O)(OR$_{aa}$)$_2$ or its anions. The term "phosphinate" refers to the radical —PR$_{aa}$(O)(OR$_{aa}$) or its anion, where each R$_{aa}$ can be selected from, for example, alkyl, alkenyl, alkynyl, aryl, arylalkyl, cycloalkyl, hydrogen, haloalkyl, heteroaryl, and heterocyclyl.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of PPAR and/or EGF receptors is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with PPAR and/or EGF receptors.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

Compounds

The disclosure provides, at least in part, compounds represented by formula I, as depicted below. Also contemplated herein are compositions that include a compound represented by formula I and e.g., a pharmaceutically or cosmetically acceptable carrier or expicient.

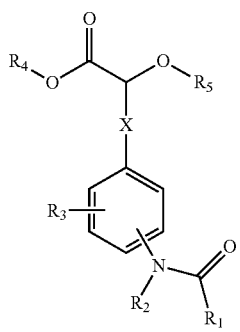

I wherein X is $C_1-C_3$alkylene, optionally substituted with one, two or three substituents selected from halogen or hydroxyl;

$R_1$ is selected from the group consisting of $C_1-C_6$alkyl, $C_3-C_6$cycloalkyl, $C_2-C_6$alkenyl, and $C_2-C_6$alkynyl;

$R_2$ is selected from the group consisting of hydrogen and $C_1-C_6$alkyl;

$R_3$ is independently selected, for each occurrence from the group consisting of hydrogen, $C_1-C_6$alkoxy, $C_1-C_6$alkyl, cyano, $C_3-C_6$cycloalkyl, halogen, hydroxyl, and nitro;

$R_4$ is selected from the group consisting of hydrogen and $C_1-C_6$alkyl;

$R_5$ is $C_1-C_6$alkyl;

or pharmaceutically acceptable salts or N-oxides thereof.

In one embodiment, $R_1$ can be $C_1-C_6$alkyl, such as methyl. In one embodiment, $R_2$ can be hydrogen. In another embodiment, $R_3$ can be selected from the group consisting of hydrogen, $C_1-C_6$alkyl, halogen, and hydroxyl. In a further embodiment, $R_3$ can be hydrogen. In one embodiment, $R_4$ and $R_5$ can each be $C_1-C_6$alkyl. In another embodiment, $R_4$ may be hydrogen and $R_5$ may be methyl. In one embodiment, X may be $(CH_2)_n$, wherein n is 1 or 2, such as 1.

In another embodiment, —NR$_2$—COR$_1$ can be in the meta position relative to X as shown in formula III.

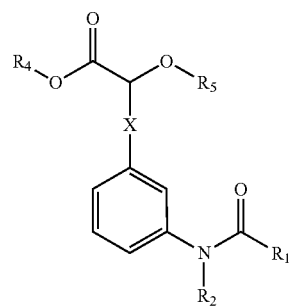

III

In another embodiment, —NR$_2$—COR$_1$ can be in the para position relative to X as shown in formula IV.

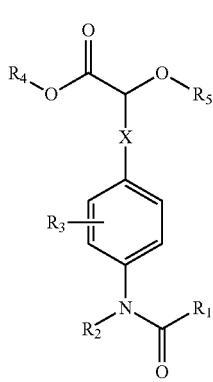

IV

The disclosure provides, at least in part, compounds represented by formula II, as depicted below. Also contemplated herein are compositions that include a compound represented by formula II and e.g., a pharmaceutically acceptable carrier.

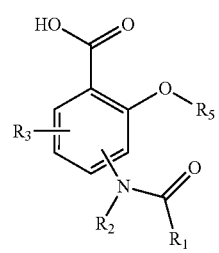

II wherein $R_1$ is selected from the group consisting of $C_1-C_6$alkyl, $C_3-C_6$cycloalkyl, $C_2-C_6$alkenyl, and $C_2-C_6$alkynyl;

$R_2$ is selected from the group consisting of hydrogen and $C_1-C_6$alkyl;

$R_3$ is independently selected, for each occurrence from the group consisting of hydrogen, $C_1-C_6$alkoxy, cyano, $C_3-C_6$cycloalkyl, halogen, hydroxyl, and nitro;

$R_5$ is hydrogen or $C_1-C_6$alkyl;

or pharmaceutically acceptable salts or N-oxides thereof.

Compounds of Formula V are also contemplated as shown below, as well as compositions that include a compound represented by formula V and e.g., a pharmaceutically acceptable carrier.

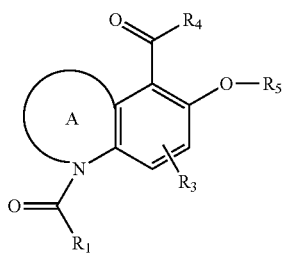

V wherein $R_1$ is selected from the group consisting of $C_1$-$C_6$alkyl, $C_3$-$C_6$cycloalkyl, $C_2$-$C_6$alkenyl, and $C_2$-$C_6$alkynyl;

$R_3$ is independently selected, for each occurrence from the group consisting of hydrogen, $C_1$-$C_6$alkoxy, cyano, $C_3$-$C_6$cycloalkyl, halogen, hydroxyl, and nitro;

$R_4$ is selected from the group consisting of hydrogen and $C_1$-$C_6$alkyl;

$R_5$ is hydrogen or $C_1$-$C_6$alkyl; and

A is a fused five or six membered heterocycle;

or pharmaceutically acceptable salts or N-oxides thereof.

In one embodiment, $R_1$ can be $C_1$-$C_6$alkyl, such as methyl. In another embodiment, $R_1$ and $R_3$ can each be $C_1$-$C_6$alkyl, such as methyl. In one embodiment, $R_2$ can be hydrogen.

In some embodiments, a compound can be represented by

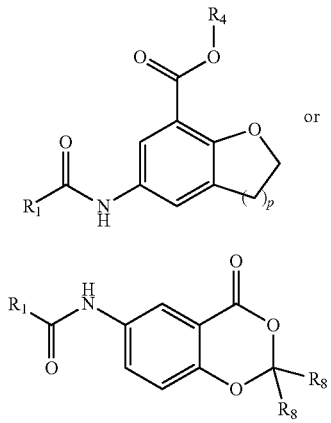

VI or

VII wherein p is 1 or 2;

$R_1$ is selected from the group consisting of $C_1$-$C_6$alkyl, $C_3$-$C_6$cycloalkyl, $C_2$-$C_6$alkenyl, and $C_2$-$C_6$alkynyl;

$R_4$ and $R_8$ are each independently selected from the group consisting of hydrogen and $C_1$-$C_6$alkyl;

or pharmaceutically acceptable salts or N-oxides thereof.

Contemplated compounds, and pharmaceutical compositions, comprising at least one compound, may be selected from the group consisting of: N-acetyl-(R)-(−)-3-(4-aminophenyl)-2-methoxypropionic acid (Compound A), N-acetyl-(S)-(−)-3-(4-aminophenyl)-2-methoxypropionic acid (Compound B), racemic N-acetyl-(S)-(−)-3-(4-aminophenyl)-2-methoxypropionic acid (compound AB);

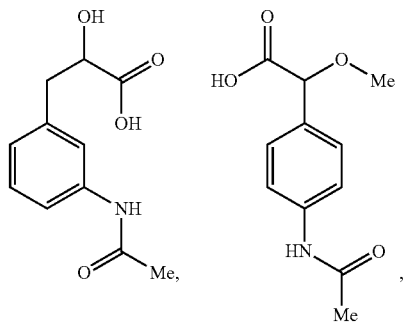

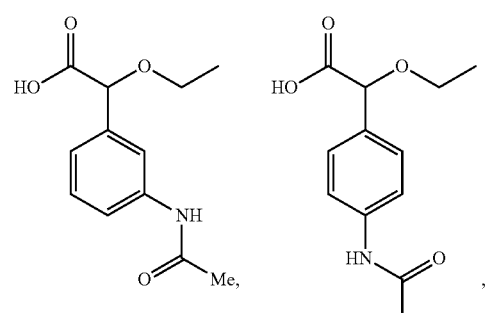

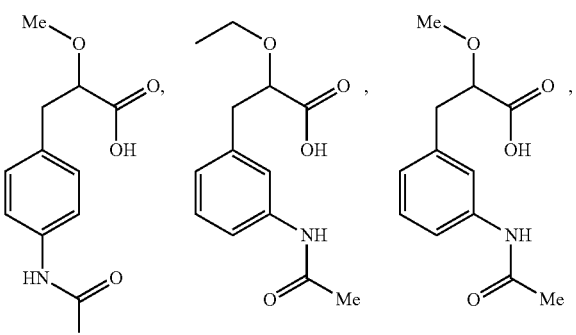

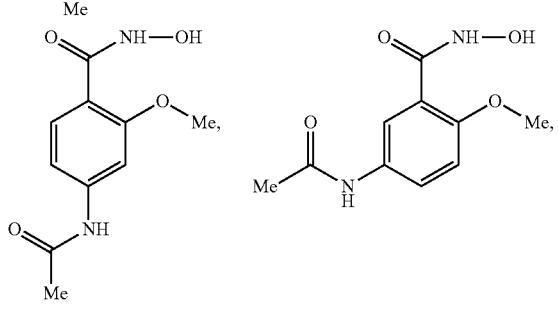

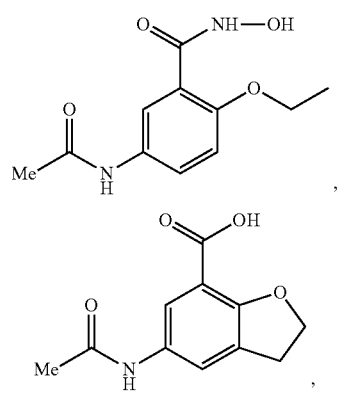

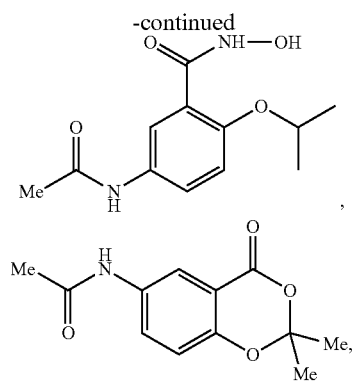

4-acetamino-N-hydroxy-2-methoxybenzamide; 1-acetyl-6-methoxy-1,2,3,4-tetrahydroquinoline-5-carboxylic acid, 5-acetamido-2hydroxybenzoic acid (e.g., acetalyated 5-aminosalicyclic acid) or pharmaceutically acceptable salts or N-oxides thereof.

The present disclosure also provides pharmaceutical compositions comprising compounds as disclosed herein formulated together with one or more pharmaceutically or cosmetically acceptable carriers. These formulations include those suitable for oral, rectal, topical, buccal and parenteral (e.g., subcutaneous, intramuscular, intradermal, or intravenous) administration, or for topical use, e.g. as a cosmetic product. Although the most suitable form of administration in any given case will depend on the degree and severity of the condition being treated and on the nature of the particular compound being used.

Therapeutic Applications

The disclosure further provides, in some embodiments, methods of modulating activity of one or more PPAR and/or EGF receptors comprising exposing said receptor to a compound of the invention. For example, provided herein are methods of treating a disease associated with expression or activity of one or more PPAR and/or EGF receptors in a patient comprising administering to the patient a therapeutically effective amount of a compound of the invention.

The disclosure is directed at least in part to treating or ameliorating hair disorders using e.g. a disclosed compound. For example, methods of stimulating hair growth is provided, wherein a disclosed compound (or e.g., a composition that includes a disclosed compound) is administered to a subject in need thereof, e.g. topically administered.

In some embodiments, a method of treating or ameliorating hair loss or hair de-pigmentation in a patient suffering from, (or anticipating suffering from) unwanted hair loss or unwanted de-pigmentation is provided, comprising administering an effective amount of a composition comprising a disclosed compound. Contemplated methods include those that slow formation of grey hair, or substantially slow hair loss, as compared to, for example, hair loss or de-pigmentation without the contemplated treatment. Methods of treating vitiligo, alopecia areata, androgenetic alopecia and/or telogenic defluvium are also contemplated.

For example, continuous sebum production can increase in acne patients; and application of a sebum inhibitor, such as disclosed herein, may be useful in the treatment of acne, seborrhea or alopecia. In another example, chronic inflammation of hair follicles (keratinocytes) can be an indication of e.g., androgenic alopecia. An inhibitor of such inflammation such as disclosed herein can be useful in e.g., the treatment of hair loss.

The compounds of the invention may be administered to subjects (animals and/or humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the compounds, formulation of compounds, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically may also include a pharmaceutically acceptable carrier or expicient.

In some embodiments, contemplated compositions may also include other agents, e.g. hair stimulating agents such as Procapil™, latanprost, minoxidil, finasteride, dutasteride, and/or spironolactone. Also contemplated herein are disclosed methods which may, in some embodiments, further comprise administering one or more hair stimulating agents, such as those above.

Contemplated compositions may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or enemas or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for transdermal or topical administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. The efficacy of treatment with the subject compositions may be determined in a number of fashions known to those of skill in the art.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The compounds disclosed herein can be prepared in a number of ways well known to one skilled in the art of organic synthesis. More specifically, compounds of the invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Example 1 Preparation of N-acetyl-(R)-(−)-3-(4-aminophenyl)-2-methoxypropionic acid (N-Acetyl E2); Compound A To (R)-(−)-3-(4-aminophenyl)-2-methoxypropionic acid (40 g) in a 0.5 L glass reactor was added ethyl acetate (80 g) and acetic anhydride (62.8 g). The mixture was stirred at 90° C. for 1 hour. Upon cooling, the solvent was removed by vacuum distillation, providing an oily residue. To this residue was added water (120 g) and ethyl acetate (120 g). After stirring for 10 min at 35° C., the layers were separated and the aqueous layer discarded. The organic layer solvent was removed by vacuum distillation. Acetone (120 g) was then added and the resulting mixture was warmed until dissolution was complete. The solution was cooled to 0° C., and the product precipitated which was collected by filtration. The solid was rinsed with acetone (20 g) and dried at 65° C. to afford 26 g of the title compound.

Example 2 In Vitro Testing in Hair Follicle Organ Culture

A Philpott model test system of microdissected organ-cultured hair follicles is used. Hair follicles and skin punches were divided into 4 groups (3 HFs/well) incubated with the test substance Compound 'A in different concentrations for 6 days. On day 0, microdissection measurements of hair length are conducted. On day 1, the medium is changed and addition of compound A (with measurement of hair length). On day 3, the medium is changed and compound a is added (with measurement of hair length). On day 6, hair length is measured and embedding occurs. FIG. 1 shows that compound A stimulates hair shaft elongating in a lower dose of compound A.

Figure 2:
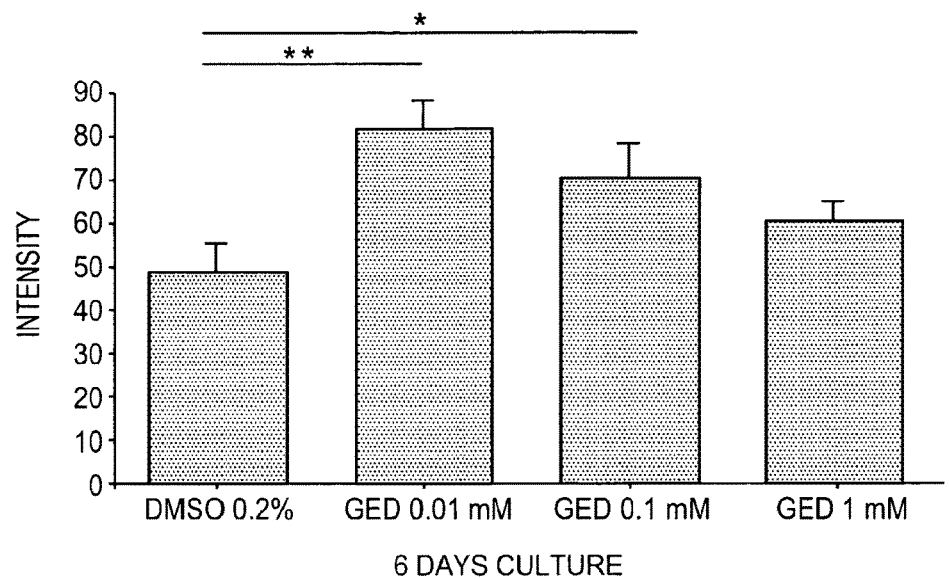
FIG. 2 depicts stimulation of human hair follicle pigmentation with various concentrations of N-acetyl E2 using Fontana-Masson histomorphometry.
Figure 3:
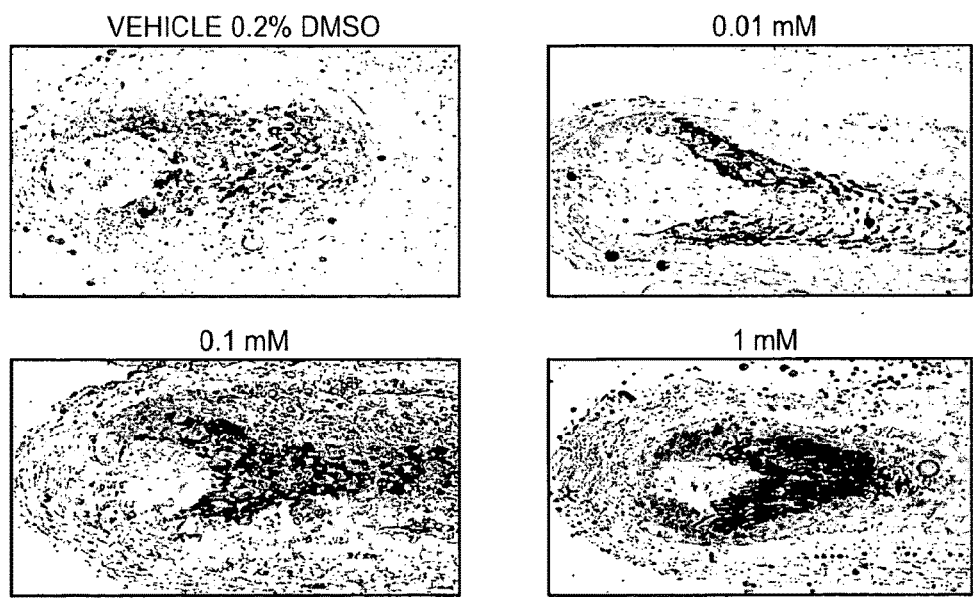
FIG. 3 hair follicle Fontana-Masson histochemistry with N-acetyl E2

Using Fontana-Massan histomorphometry/melanin staining on cryosections, FIG. 2 shows the stimulation of human hair follicle pigmentation by compound A. FIG. 3 depicts a Fontana-Masson histochemistry of hair follicle on use of compound A.

Figure 4:
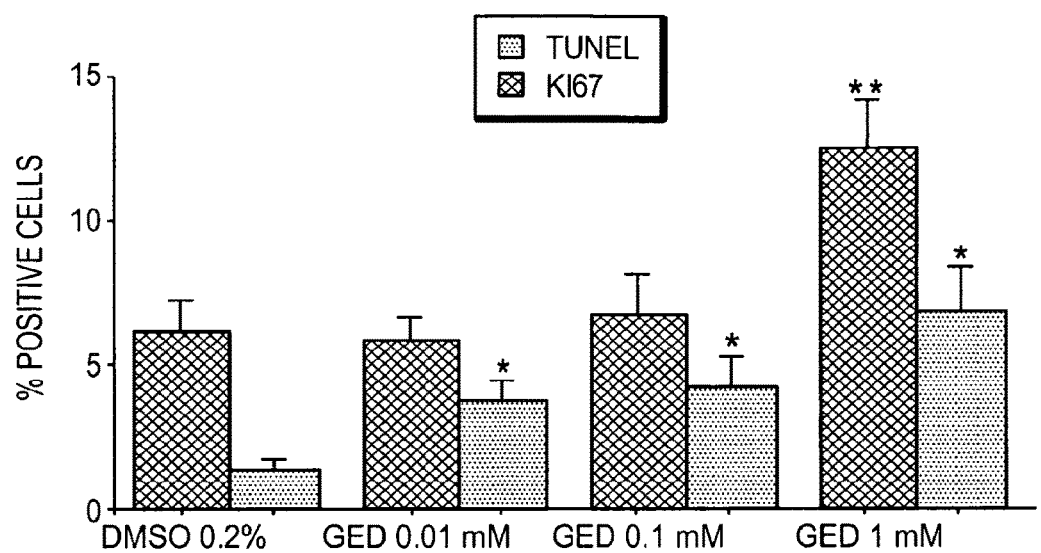
FIG. 4 depicts the observed follicle Ki67/Tunel immunohistomorphometry with N-acetyl E2.

Ki-67/Tunel staining was also conduct on the hair follicles using fluorescent staining. FIG. 4 depicts the follicle Ki67/Tunel immunohistomorphometry, and indicates that high doses of compound A stimulates both proliferation and apoptosis of human hair matrix keratinocytes.

Figure 5:
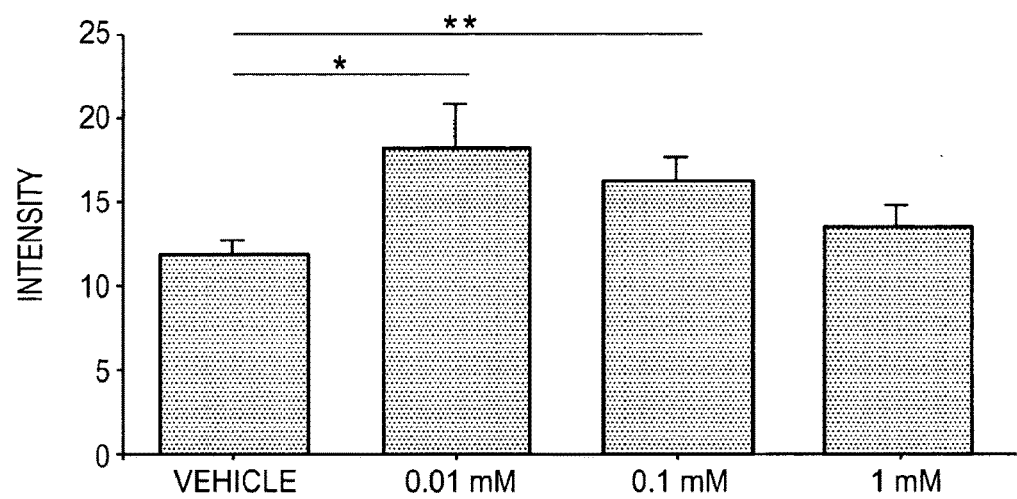
FIG. 5 depicts K15 expression in hair follicles treated with compound A.
Figure 6:
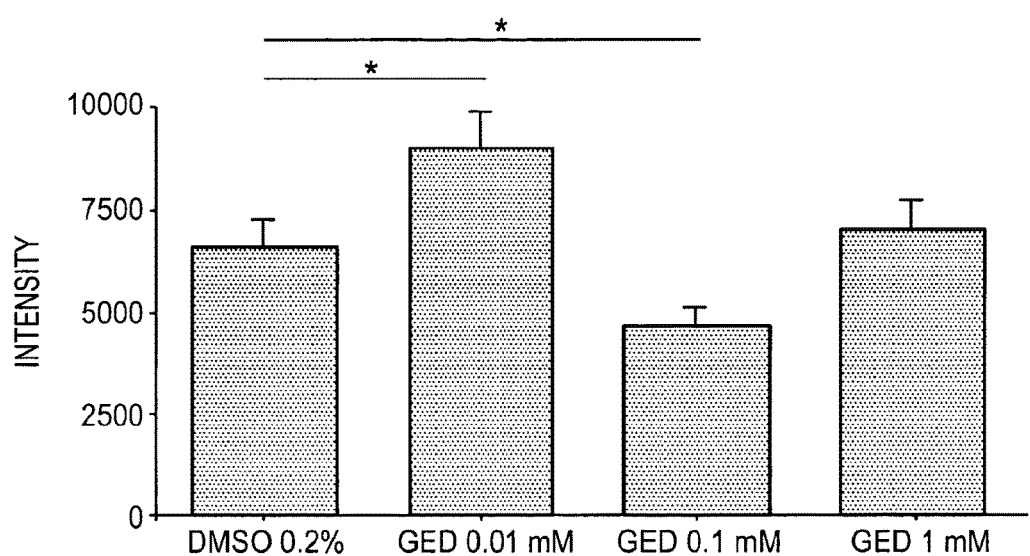
FIG. 6 depicts regulation of K19 cells in hair follicles treated with compound A.

There is significant upregulation of K15 expression in the lower hair follicle in lower doses of compound A, while treated skin shows no measurable expression (see FIG. 5). FIG. 6 indicates significant upregulation of K19 cless in the lower hair follicle for lower concentration, while the 10× higher concentration shows down regulation (FIG. 6). The skin shows no measurable expression.

Example 3 Keratinocytes

Figure 7:
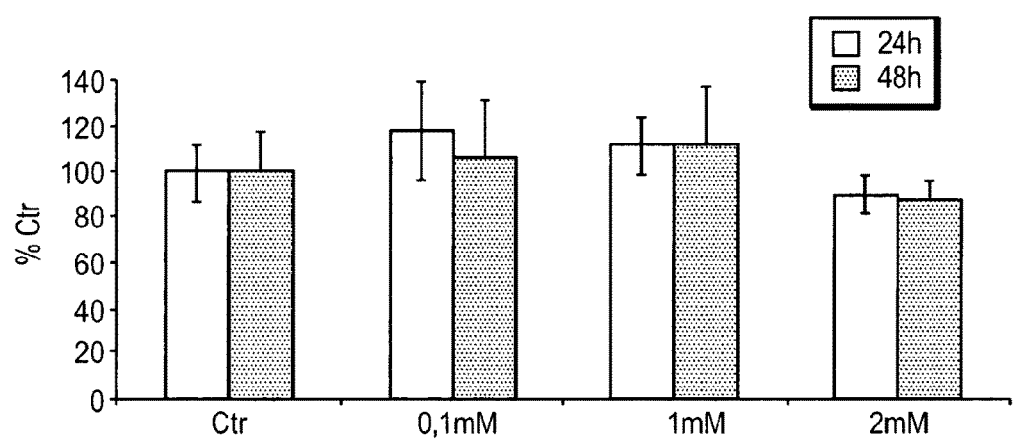
FIG. 7 depicts effects of a disclosed compound on human keratinocytes.

To assess the possible toxic or cytostatic effect of the substances under study, a spectrophotometric test (MTT) was carried out. The human primary keratinocytes, isolated from skin biopsies, were plated in wells of a 24-well plate in suitable medium with addition of antibiotics, calcium, and specific growth factors. At around 70% confluence, the cells were exposed to the presence of Compound A, at various concentrations (0.1-1-2 mM), for 24 and 48 h in suitable medium with addition of antibiotics, calcium, but no growth factors. This culture condition was done for all the subsequent experiments. At the end of the treatment, the MTT test was done. The results are indicated in FIG. 7. Compound A in all concentrations used did not show any effect on cellular vitality.

Example 4 TNF Alpha

Figure 8:
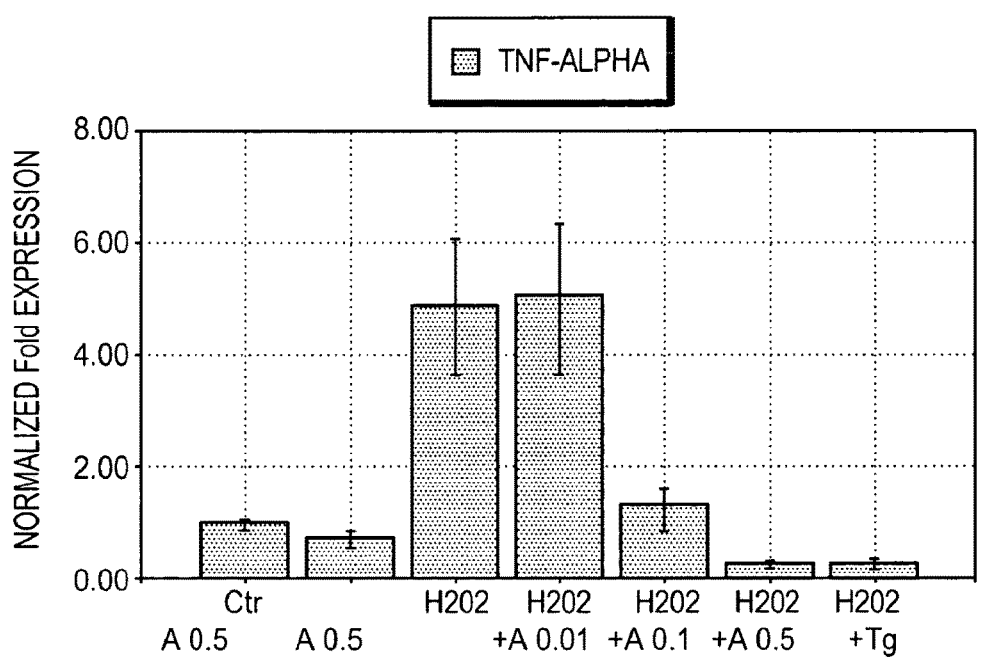
FIG. 8 depicts inhibition of TNF alpha by $H_2O_2$ and a disclosed compound.

Analysis of the inhibition of compound A of the mRNA induction of the proinflammatory cytokine TNF-alpha by $H_2O_2$ was carried out by Real time RT-PCR. The keratinocytes were plated in dishes of 6 cm/Ø. At 80% confluence, the cells were treated with $H_2O_2$ (300 μM) in presence of Compound A at the three concentrations (0.01-0.1-0.5 mM) for 6 h. At the end of the treatment, the cells were lysed in a lysis buffer and subjected to isolation and subsequent retrotranscription of the RNA. Compound A proved able to inhibit the expression of the mRNA of TNF-α induced by $H_2O_2$ at the two higher doses (0.1 mM; 0.5 mM). The higher dose demonstrated a complete inhibition of the proinflammatory cytokine with an effect similar to troglitazone (Tg). (FIG. 8)

Example 5 Inhibition of mRNA Expression of IL-6 Induced by Presence of IFN-γ

Analysis of the inhibition by compound A of the mRNA induction of the proinflammatory cytokine IL-6 by IFN-γ was done through Real time RT-PCR. The keratinocytes were plated in dishes of 6 cm/Ø.

Figure 9:
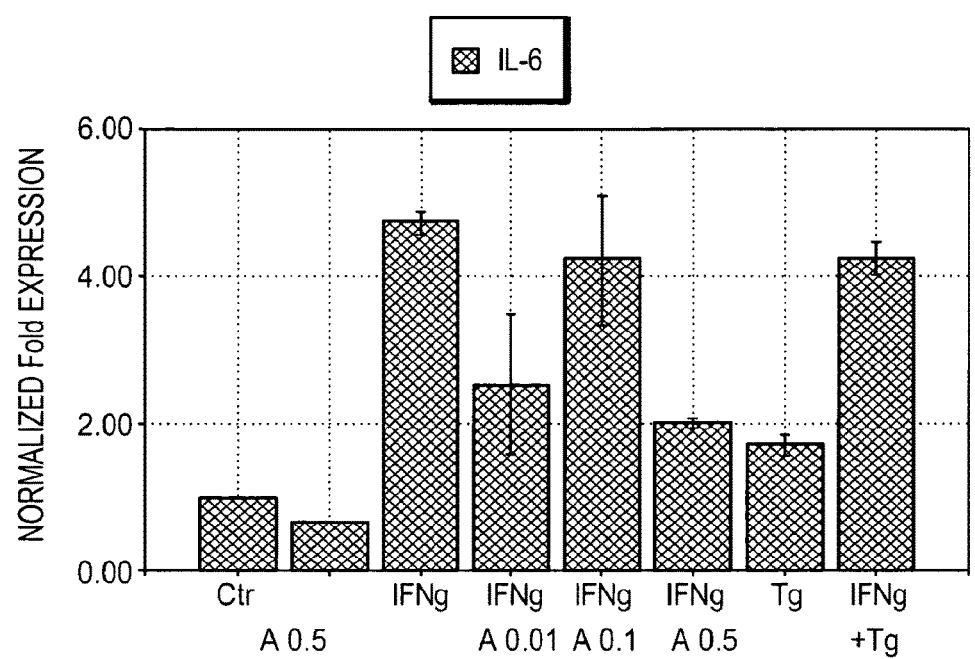
FIG. 9 depicts inhibition on mRNA expression of IL-6 induced by the presence of IFN-gamma.

At 80% confluence, the cells were treated with IFN-γ (30 ng/ml) in presence of compound A at the three concentrations (0.01-0.1-0.5 mM) for 6 h. At the end of the treatment, the cells were lysed in a lysis buffer and subjected to isolation and subsequent retrotranscription of the RNA The results (as shown in FIG. 9) reveal the ability of Compound A to inhibit the expression of the inflammatory cytokine induced by presence of IFN-γ which does not appear to be dose-dependent.

Example 6 Inhibitory Capacity on the Activation of Nuclear Factor NF-kB Induced by Presence of $H_2O_2$ Evaluation of the inhibition by compound A of the activation of nuclear transcription factor NF-kB induced by the presence of $H_2O_2$ was done by analysis in cytofluorimetry.

Figure 10:
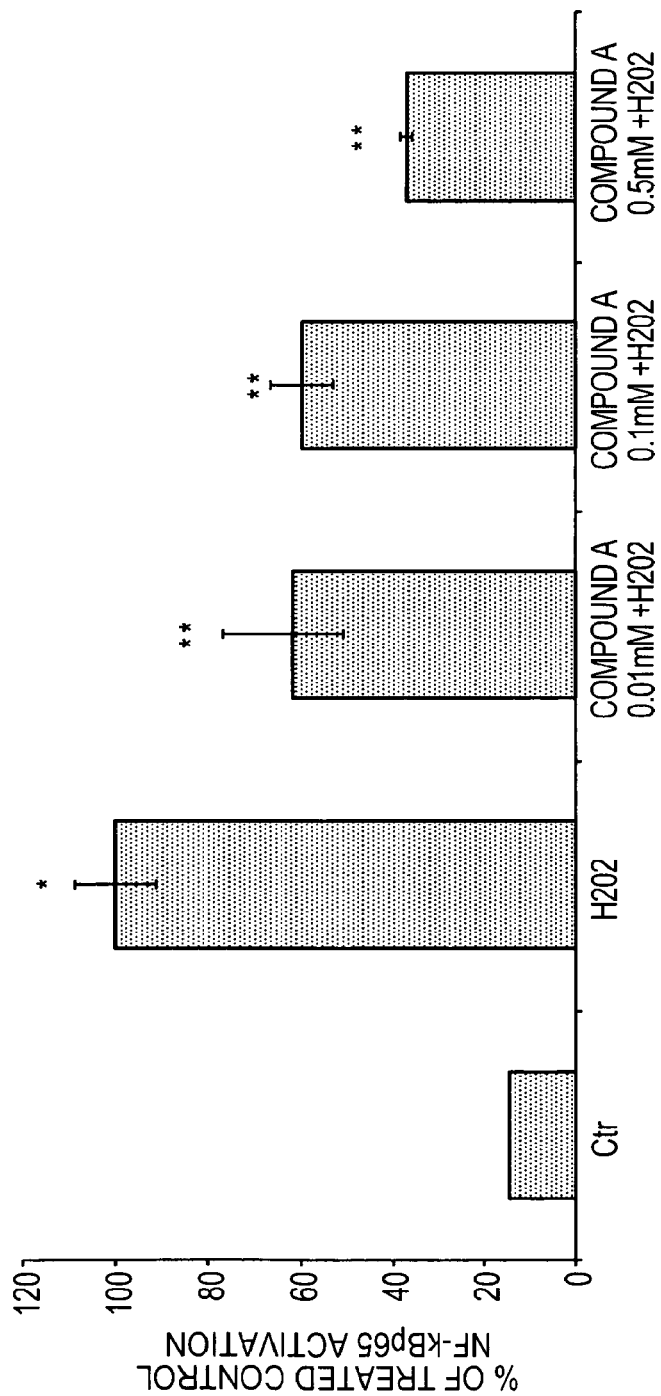
FIG. 10 depicts inhibition of a disclosed compound on the activation of NF-kB.

The keratinocytes were plated in wells of a 12-well plate. At 80% confluence, the cells were treated with $H_2O_2$ (300 μM) in presence of compound A at the three concentrations (0.01-0.1-0.5 mM) for 1 h. At the end of the treatment, the cells were fixed in paraformaldehyde, permeabilized in methanol and then incubated in presence of the specific antibody of subunit p65. Compound A revealed an inhibitory effect on the activation and subsequent translocation of NF-kB in dose-dependent manner (FIG. 10).

Example 7 Inhibition of Protein Expression of IL-6 Induced by Presence of LPS

Figure 11:
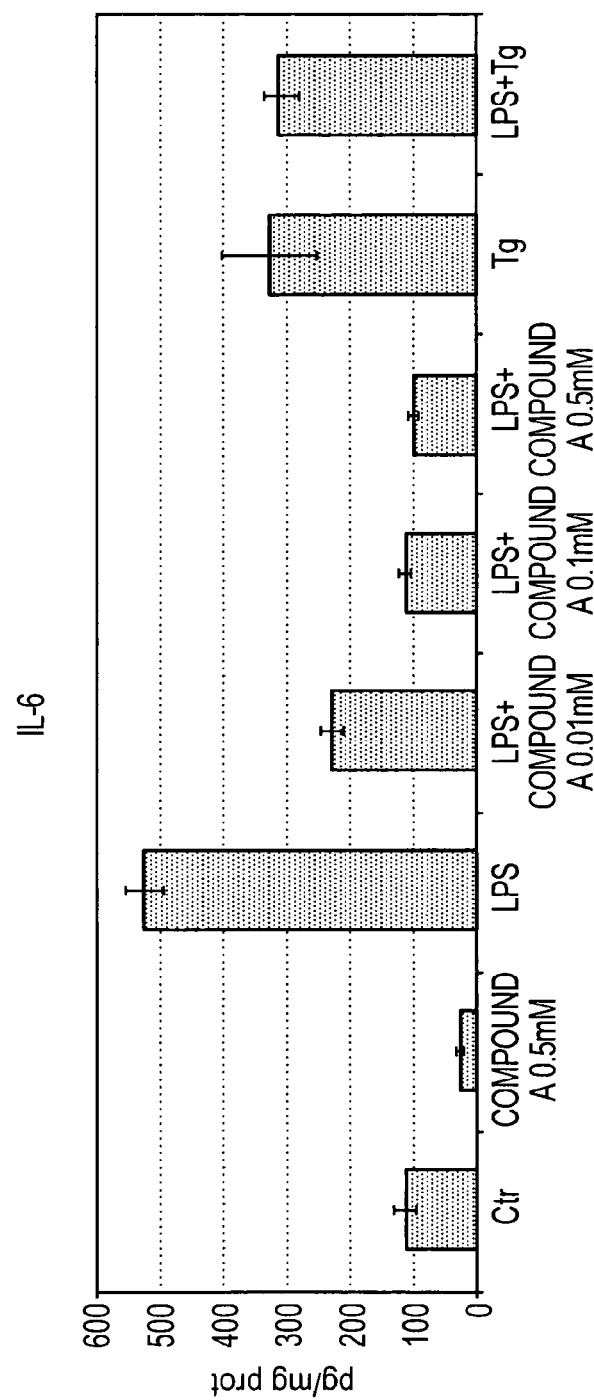
FIG. 11 depicts inhibition of a disclosed compound on protein expression of IL-6 induced by presence of LPS.

Analysis of the inhibition by Compound A of the protein induction of IL-6 by LPS (lipopolysaccharide) was done with the ELISA kit. The keratinocytes were plated in wells of a 24-well plate. At 80% confluence, the cells were treated with LPS (10 μg/ml) in presence of compound A at the three concentrations (0.01-0.1-0.5 mM) for 24 h. At the end of the treatment, the supernatant was decanted, centrifuged so as to remove any cell detritus, and kept at −80° C. until the time of the analysis. The quantity of IL-6 present in the supernatant was normalized by the protein concentration of the sample itself. The results (FIG. 11) revealed the ability of compound A to inhibit, in dose-dependent manner, the protein expression of the inflammatory cytokine under study.

Example 8 Human Sebocytes

Figure 12:
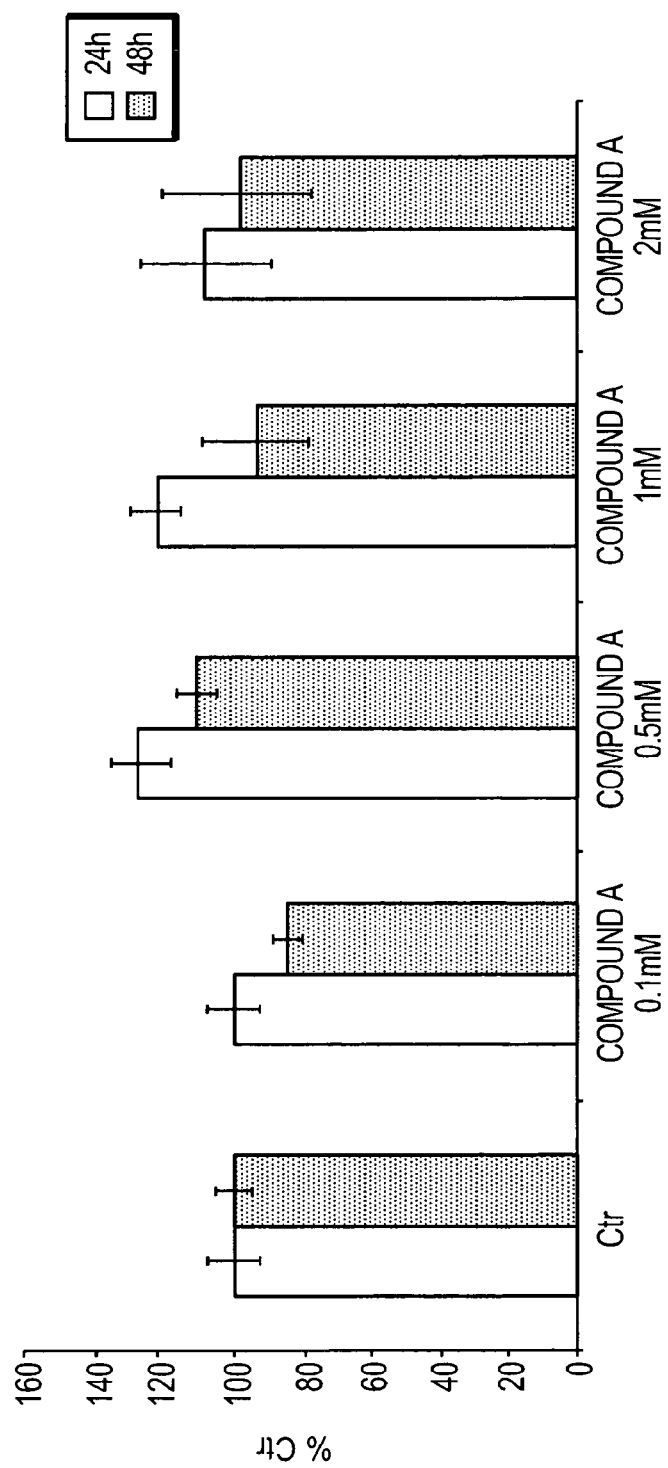
FIG. 12 depicts effect of a disclosed compound on human sebocytes.

To assess the possible toxic or cytostatic effect of the substances under study, a spectrophotometric test (MTT) was carried out. The sebocytes were plated in wells of a 24-well plate in suitable medium with addition of antibiotics, calcium and EGF. At roughly 70% confluence, the cells were exposed to the presence of compound A, in various concentrations (0.1-0.5-1-2 mM), for 24 and 48 h. At the end of the treatment, the MTT test was performed. Compound A in all concentrations used demonstrated no effects on cell vitality. (FIG. 12)

Example 9 Evaluation of the Inhibitory Capacity of a Compound on Sebogenesis Induced by Stimuli of Lipid Type (Linoleic Acid, Testosterone)

Figure 13:
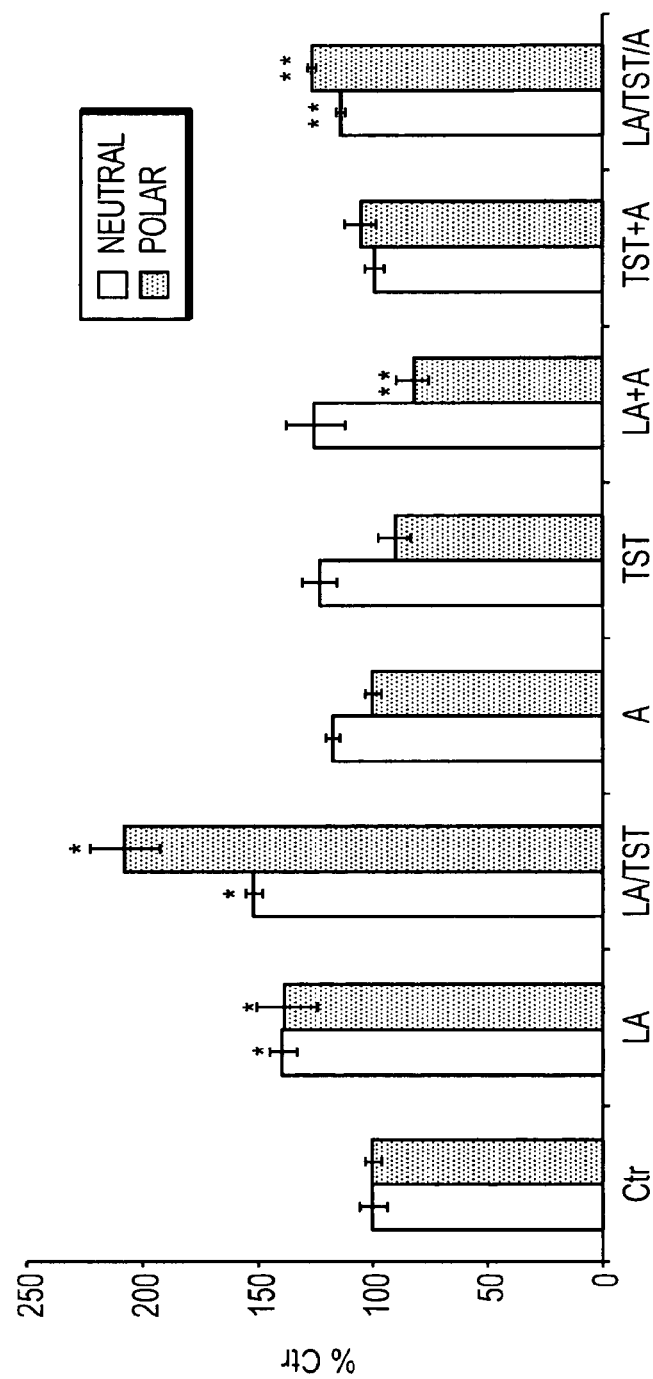
FIG. 13 depicts inhibitory capacity of a disclosed compound on sebogenesis induced by lipid type stimulus.

Analysis of the inhibition by (compound A) of sebogenesis induced by treatment with linoleic acid (LA) and with testosterone (TST) was evaluated by spectrofluorimetry, using Nile Red as selective marker of intracellular lipids (Nile Red Assay). The sebocytes were plated in wells of a 24-well plate. Next day, they were deprived of serum (2%) and after 24 h they were stimulated, for another 24 h, with LA (10-4M), TST (20 nM) in presence or in absence of A (1 mM). At the end of the treatment, the sebocytes were stained with Nile Red. The quantitative analysis was done by spectrofluorimetry, which made it possible to distinguish between neutral lipids and polar lipids based on the different wavelength of excitation and emission. The data obtained revealed that the treatment with LA is able to induce lipid synthesis and that the combined LA+TST treatment further increases this effect. The presence of Compound A proved able to reduce the lipidogenic stimulus. (FIG. 13).

Figure 14A:
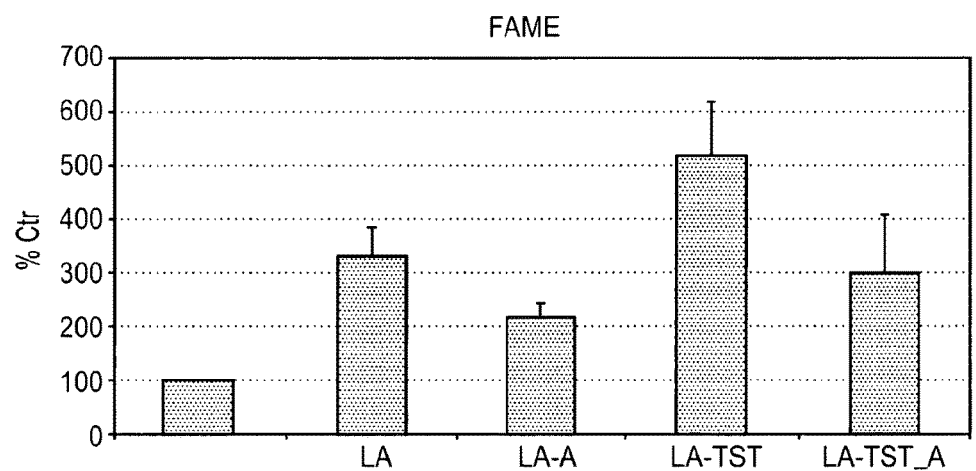
FIG. 14A depicts the results of a fatty acid assay and FIG. 14B depicts the results of a squalene analysis of sebogenesis inhibition.
Figure 14B:
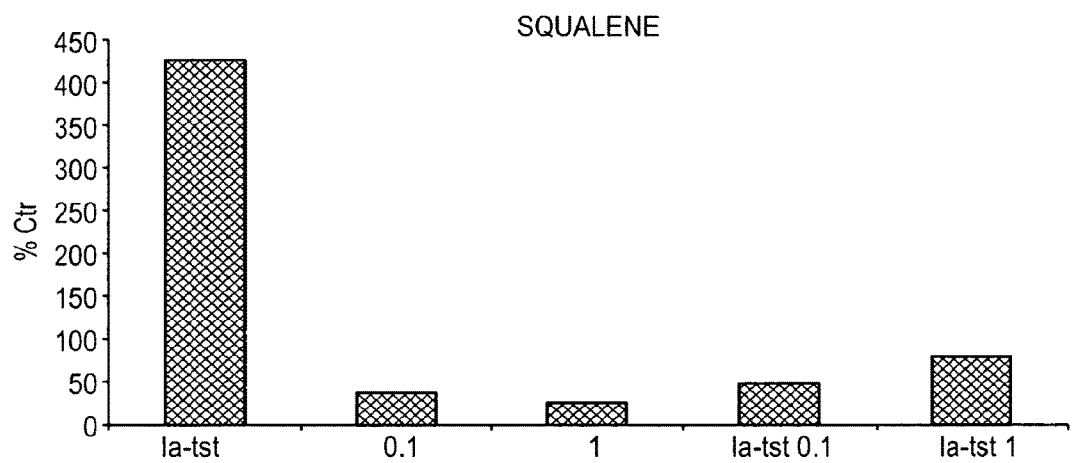

Example 10 Evaluation of the Inhibitory Capacity on Sebogenesis Induced by Stimuli of Lipid Type (Linoleic Acid, Testosterone): Evaluation of Fatty Acids and Squalene In order to evaluate in greater detail the inhibition by Compound A of sebogenesis induced by LA and TST, assays were performed on the lipid extract of the sebocytes using gas chromatography coupled with mass spectrometry (GC-MS). The sebocytes were treated by the scheme described for the Nile Red assay. At the end of the treatment, the cells were removed and then the lipid extraction was done by using organic solvents. One part of the extract was used to analyze the fatty acid composition, while the other part was used for the determination of the quantity of squalene, a lipid characteristic of sebum. The fatty acid assay showed that the lipidogenic stimulus induced by the treatment with LA and LA+TST was reduced by the presence of A (FIG. 14A). These results are confirmed by the squalene analysis. (FIG. 14B)

Example 11 Evaluation of the Inhibitory Capacity on Sebogenesis Induced by Stimuli of Lipid Type (Linoleic Acid, Testosterone)

Figure 15:
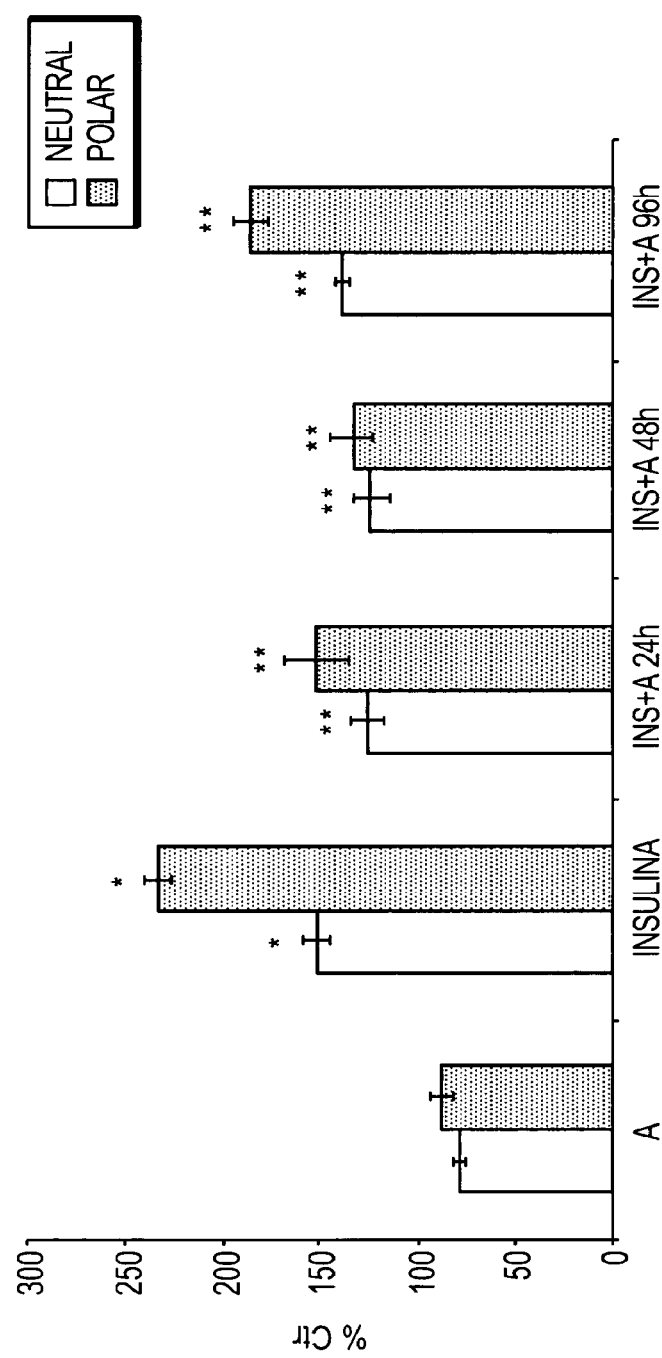
FIG. 15 depicts treatment with linoleic acid and testosterone with lipidogenic stimulus.

Analysis of the inhibition by compound A of sebogenesis induced by treatment with linoleic acid (LA) and with testosterone (TST) was evaluated by spectrofluorimetry, using Nile Red as selective marker of intracellular lipids (Nile Red Assay). The sebocytes were plated in wells of a 24-well plate. Next day, they were deprived of serum (2%) and after 24 h they were stimulated, for another 24 h, with LA (10-4M), TST (20 nM) in presence or in absence of compound A (1 mM). At the end of the treatment, the sebocytes were stained with Nile Red. The quantitative analysis was done by spectrofluorimetry, which made it possible to distinguish between neutral lipids and polar lipids based on the different wavelength of excitation and emission. The data obtained (FIG. 15) revealed that the treatment with LA is able to induce lipid synthesis and that the combined LA+TST treatment further increases this effect. The presence of A proved able to reduce the lipidogenic stimulus. No differences were observed in regard to the times of treatment with the A.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method for modulating hair growth in a human subject in need thereof, the method comprising administering topically to the human subject a therapeutically effective amount of a pharmaceutically and/or cosmetically acceptable composition comprising:
   N-acetyl-(S)-3-(4-aminophenyl)-2-methoxypropionic acid, or a pharmaceutically acceptable salt or an N-oxide thereof; and
   an excipient.

2. The method of claim 1, wherein the composition further comprises a hair stimulating agent.

3. The method of claim 1, wherein the method further comprises administering a hair stimulating agent.

4. A method for treating or ameliorating limited hair growth, short hair growth, or hair loss in a human subject in need thereof, the method comprising administering topically to the human subject a therapeutically effective amount of a pharmaceutically and/or cosmetically acceptable composition comprising:
   N-acetyl-(S)-3-(4-aminophenyl)-2-methoxypropionic acid, or a pharmaceutically acceptable salt or an N-oxide thereof; and
   an excipient.

5. The method of claim 4, wherein the composition further comprises a hair stimulating agent.

6. The method of claim 4, wherein the method further comprises administering a hair stimulating agent.

7. A method for treating or ameliorating alopecia in a human subject in need thereof, the method comprising administering topically to the human subject a therapeutically effective amount of a pharmaceutically and/or cosmetically acceptable composition comprising:
   N-acetyl-(S)-3-(4-aminophenyl)-2-methoxypropionic acid, or a pharmaceutically acceptable salt or an N-oxide thereof; and
   an excipient.

8. The method of claim 7, wherein the alopecia is anagen alopecia.

9. The method of claim 7, wherein the alopecia is telogen alopecia.

10. The method of claim 7, wherein the alopecia is alopecia areata.

11. The method of claim 8, wherein the composition further comprises a hair stimulating agent.

12. The method of claim 9, wherein the composition further comprises a hair stimulating agent.

13. The method of claim 10, wherein the composition further comprises a hair stimulating agent.

14. The method of claim 8, wherein the method further comprises administering a hair stimulating agent.

15. The method of claim 9, wherein the method further comprises administering a hair stimulating agent.

16. The method of claim 10, wherein the method further comprises administering a hair stimulating agent.

* * * * *